(12) United States Patent
Hamdouchi et al.

(10) Patent No.: US 8,822,486 B2
(45) Date of Patent: Sep. 2, 2014

(54) SPIROPIPERIDINE COMPOUNDS

(75) Inventors: Chafiq Hamdouchi, Carmel, IN (US); Jayana Pankaj Lineswala, Brownsburg, IN (US); Pranab Maiti, Bangalore (IN)

(73) Assignee: Eli Lilly and Company, Indianapolis, IN (US)

(*) Notice: Subject to any disclaimer, the term of this patent is extended or adjusted under 35 U.S.C. 154(b) by 317 days.

(21) Appl. No.: 13/505,470

(22) PCT Filed: Nov. 19, 2010

(86) PCT No.: PCT/US2010/057359
§ 371 (c)(1),
(2), (4) Date: May 2, 2012

(87) PCT Pub. No.: WO2011/066183
PCT Pub. Date: Jun. 3, 2011

(65) Prior Publication Data
US 2012/0220616 A1    Aug. 30, 2012

Related U.S. Application Data

(60) Provisional application No. 61/265,181, filed on Nov. 30, 2009.

(51) Int. Cl.
C07D 471/10 (2006.01)
C07D 417/06 (2006.01)
C07D 409/06 (2006.01)
C07D 413/06 (2006.01)
C07D 405/06 (2006.01)

(52) U.S. Cl.
CPC ............ *C07D 409/06* (2013.01); *C07D 413/06* (2013.01); *C07D 471/10* (2013.01); *C07D 417/06* (2013.01); *C07D 405/06* (2013.01)
USPC .................. 514/278; 546/17; 546/18

(58) Field of Classification Search
CPC .. C07D 409/06; C07D 413/06; C07D 471/10; C07D 417/06; C07D 405/06
USPC ...................... 514/278; 546/17, 18
See application file for complete search history.

(56) References Cited

U.S. PATENT DOCUMENTS

2006/0183904 A1  8/2006  Guo et al.
2009/0170908 A1  7/2009  Shimada et al.
2012/0004165 A1  1/2012  Keil et al.
2012/0004166 A1  1/2012  Keil et al.

FOREIGN PATENT DOCUMENTS

EP       1731505       12/2006
WO    2011046851       4/2011

OTHER PUBLICATIONS

Yoshizumi, et al., "Design, synthesis, and structure-activity relationship study of a novel class of ORL1 eceptor antagonists based on N-biarylmethyl spiropiperidine," Bioorganic & Medicinal Chemistry Letters, vol. 18, pp. 3778-3782 (2008).

Briscoe, et al., "The Orphan G Protein-coupled Receptor GPR40 is Activated by Medium and Long Chain Fatty Acids," The Journal of Biological Chemistry, vol. 278, No. 13, pp. 11303-11311 (2003).

Itoh, et al., "Free fatty acids regulate insulin secretion from pancreatic b cells through GPR40," Nature, vol. 422, pp. 173-176 (2003).

Kotarsky, et al., "A human cell surface receptor activated by free fatty acids and thiazolidinedione drugs," Biochemical and Biophysical Research Communications, vol. 301, pp. 406-410 (2003).

Tomita, et al., "GPR40 gene expression in human pancreas and insulinoma," Biochemical and Biophysical Research Communications, vol. 338, pp. 1788-1790 (2005).

Tomita, et al., "Expression of the gene for a membrane-bound fatty acid receptor in the pancreas and islet cell tumours in humans: evidence for GPR40 expression in pancreatic beta cells and implications for insulin secretion," Diabetologia, vol. 49, pp. 962-968 (2006).

Nagasumi, et al., "Overexpression of GPR40 in Pancreatic Beta Cells Augments Glucose-Stimulated Insulin Secretion and Improves Glucose Tolerance in Normal and Diabetic Mice," Diabetes, vol. 58, pp. 1067-1076 (2009).

*Primary Examiner* — Bong-Sook Baek
(74) *Attorney, Agent, or Firm* — MaCharri Vorndran-Jones

(57)         ABSTRACT

A compound of the formula: or a pharmaceutically acceptable salt thereof as well as a pharmaceutical composition, and a method for treating diabetes.

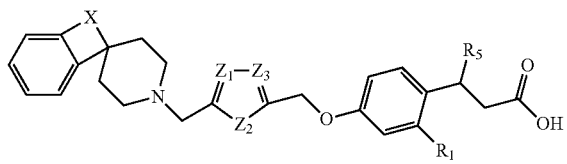

20 Claims, No Drawings

SPIROPIPERIDINE COMPOUNDS

REFERENCE TO RELATED APPLICATION

This application is submitted as a United States national phase entry, pursuant to 35 U.S.C. §371, of PCT/US2010/057359, filed on Nov. 19, 2010, which claims the benefit of U.S. provisional patent application Ser. No. 61/265,181, filed Nov. 30, 2009, each of which is incorporated by reference herein.

Administration of currently approved medicines for the treatment of diabetes has been associated with undesired adverse effects that sometimes include hypoglycemia, liver damage, gastrointestinal disease, weight gain, or other undesired effects that may be associated with the PPAR gamma activity.

GPR40 is a G protein-coupled receptor which is reported as predominately expressed at high levels in rodent pancreatic beta cells, insulinoma cell lines, and human islets. This receptor is activated by medium and long-chain fatty acids, and thus the receptor is also known as FFAR1 (Free Fatty Acid Receptor 1). The glucose dependency of insulin secretion is an important feature of activating GPR40, making this receptor an excellent target for developing efficacious for use in the treatment of type 2 diabetes ("T2D").

A recently published US Patent application, US 2009/0170908 A1 ("'908"), generally discloses compounds having a hydrocarbon spiro group feature and are stated to have activity as G protein-coupled receptor 40 ("GPR40") modulators. The compounds of the '908 disclosure are compounds requiring a hydrocarbon spiro group that is free of heteroatoms in the spiro feature. In contrast, many of the presently claimed spiropiperidine compounds provide desired selective activation of GPR40 without detectible PPAR activity.

Compounds of this invention are potent activators of GPR40. This invention provides a desired novel treatment option acting through a pharmacological mechanism that is unique compared to commercially available treatments and further provides compounds that selectively activate GPR40 as compared to PPAR gamma. The pharmacological profile of compounds of this invention, as selective GPR40 activators, can be particularly desirable for use in the treatment of T2D. Additionally, the selective GPR40 modulation may provide a particularly desirable safety profile for use in the treatment of T2D by avoiding effects associated with PPAR gamma modulation.

The present invention is directed to compounds of the formula:

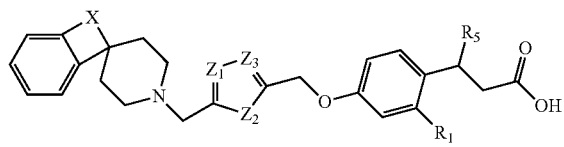

I or a pharmaceutically acceptable salt thereof;
wherein:
$R_1$ is selected from the group consisting of H, F and Cl;
$R_5$ is H or —C≡CCH$_3$;
X is selected from the group consisting of —CH$_2$CH$_2$—, —CH=CH—, and —N(R$_7$)CH$_2$—;
$R_7$ is selected from the group consisting of H and C$_{1-3}$alkyl;
$Z_1$ is selected from the group consisting of —C(R$_3$)— and —N—;
$R_3$ is selected from the group consisting of H, OCH$_3$, and CH$_3$;
$Z_2$ is selected from the group consisting of —S— and —O—;
$Z_3$ is selected from the group consisting of —C(R$_4$)— and —N—;
$R_4$ is selected from the group consisting of H, OCH$_3$, and CH$_3$; and
wherein at least one selected from the group consisting of $Z_1$ and $Z_3$ is —C(R$_3$)— or —C(R$_4$)—.

A further embodiment of this invention provides the use of a compound as claimed by the present invention or a pharmaceutically acceptable salt thereof for use in the manufacture of a medicament. Another embodiment of the invention is wherein the medicament is for use in the treatment of diabetes. A further embodiment of this invention is the use of a compound as claimed herein or a pharmaceutically acceptable salt thereof for use as a therapy. A further embodiment of the invention is a compound as claimed by the present invention, or a pharmaceutically acceptable salt thereof for use in the treatment of diabetes. Further, the invention relates to a compound as claimed by the present invention for use as a medicament.

A further embodiment of this invention provides a method for treating diabetes in a mammal, comprising the step of administering to the mammal a compound as claimed by the present invention or a pharmaceutically acceptable salt thereof.

In another embodiment, the present invention also relates to pharmaceutical compositions comprising a compound as claimed by the present invention, or a pharmaceutically acceptable salt thereof, and a pharmaceutically acceptable carrier. A further embodiment is a pharmaceutical composition of the present invention further comprising a second pharmaceutical agent.

In a preferred embodiment of the invention compounds of this invention selectively activate GPR40 relative to PPAR gamma. Relative IC$_{50}$s for PPAR activity of exemplified compounds are generally greater than 10 µM, supporting that such compound does not activate PPAR isoforms.

When $R_5$ is —C≡CCH$_3$ compounds of Formula I have a chiral center. The present invention contemplates both the racemic compounds as well as individual isomeric forms. When $R_5$ is —C≡CCH$_3$ then the S isomer is generally preferred.

Compounds of Formula I wherein $R_5$ is —C≡CCH$_3$ are preferred. Additionally, compounds wherein $R_5$ is H and $R_1$ is F are preferred. Compounds wherein $R_1$ is H are preferred when $R_5$ is —C≡CCH$_3$. Compounds wherein X is selected from —CH$_2$CH$_2$— and —CH=CH— are preferred. Compounds wherein X is —CH=CH— are preferred. Compounds wherein $Z_2$ is —S— are preferred. Compounds wherein $Z_1$ is —C(R$_3$)— are preferred. Compounds wherein $Z_3$ is —C(R$_4$)— are preferred. Compounds wherein $R_3$ is selected from H and CH$_3$ are preferred. Compounds wherein $R_4$ is H are preferred. Compounds wherein X is —N(CH$_3$)CH$_2$— are preferred.

Another embodiment of this invention provides compounds of Formula I or a pharmaceutically acceptable salt thereof, wherein:
$R_1$ is H; $R_5$ is —C≡CCH$_3$; —X is —CH=CH—, $Z_2$ is —S—.

Another embodiment of this invention provides compounds of Formula I or a pharmaceutically acceptable salt thereof, wherein:
$R_1$ is H; $R_5$ is —C≡CCH$_3$; —X is —CH=CH—, $Z_2$ is —S—; $Z_1$ is —C(R$_3$)—; $Z_3$ is —C(R$_4$)—.

Another embodiment of this invention provides compounds of Formula I or a pharmaceutically acceptable salt thereof, wherein:

$R_1$ is H; $R_5$ is —C≡CCH$_3$; —X is —CH=CH—, $Z_2$ is —S—; $Z_1$ is —C($R_3$)—; $Z_3$ is —CH—.

Another embodiment of this invention provides compounds of Formula I or a pharmaceutically acceptable salt thereof, wherein:
$R_1$ is F or Cl; $R_5$ is H; X is —CH=CH—; $Z_2$ is —S—.

Another embodiment of this invention provides compounds of Formula I or a pharmaceutically acceptable salt thereof, wherein:
$R_1$ is F; $R_5$ is H; X is —CH=CH—; $Z_2$ is —S—; $Z_1$ is —C($R_3$)—; $Z_3$ is —C($R_4$)—.

Another embodiment of this invention provides compounds of Formula I or a pharmaceutically acceptable salt thereof, wherein:
$R_1$ is F or Cl when $R_5$ is H;

Another embodiment of this invention provides compounds of Formula I or a pharmaceutically acceptable salt thereof, wherein:
$R_1$ is H; $R_5$ is —C≡CCH$_3$; $Z_2$ is —S— and X is —CH=CH— or —N(CH$_3$)CH$_2$—.

Another embodiment of this invention provides compounds of Formula I or a pharmaceutically acceptable salt thereof, wherein:
$R_1$ is H; $R_5$ is —C≡CCH$_3$; $Z_2$ is —S— and X is —CH=CH— or —N(CH$_3$)CH$_2$—; $Z_1$ is —C($R_3$)—; $Z_3$ is —CH—.

Another preferred embodiment of this invention is the S-isomer of the compound of Formula I wherein $R_5$ is —C≡CCH$_3$.

A preferred embodiment of this invention is a compound of the formula:

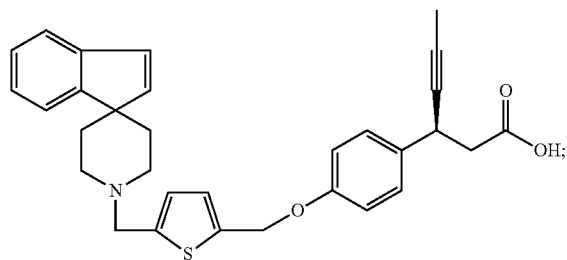 [SMILES: CC#C[C@@H](CC(=O)O)c1ccc(OCc2ccc(CN3CCC4(C=Cc5ccccc54)CC3)s2)cc1]

or a pharmaceutically acceptable salt thereof.

The compounds of the present invention are preferably formulated as a pharmaceutical composition administered by a variety of routes. Most preferably, such compositions are for oral administration. Such pharmaceutical compositions and processes for preparing same are well known in the art. See, e.g., Remington: The Science and Practice of Pharmacy (A. Gennaro, et al., eds., 21st ed., Mack Publishing Co., 2005).

"Pharmaceutically-acceptable salt" refers to salts of the compounds of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The term "pharmaceutically acceptable carrier" means that the carrier, diluent, excipients, and salt are pharmaceutically compatible with the other ingredients of the composition.

The abbreviations used herein are defined according to *Aldrichimica Acta*, Vol. 17, No. 1, 1984. Other abbreviations are defined as follows: "Prep" refers to preparation; "Ex" refers to example; "min" refers to minute or minutes; "ADDP" refers to 1,1'-(azodicarbonyl)dipiperidine; "DCM" refers to dichloromethane; "EtOAc" refers to ethyl acetate; "THF" refers to tetrahydrofuran; "$T_R$" refers to retention time; "IC$_{50}$" refers to the concentration of an agent that produces 50% of the maximal inhibitory response possible for that agent; "DMEM" refers to Dulbecco's Modified Eagle's Medium; "DTT" refers to dithiothreitol; "F12" refers to Ham's F12 medium; "FBS" refers to Fetal Bovine Serum; "HEK" refers to human embryonic kidney; "PPAR" refers to peroxisome proliferator-activated receptor; "PPRE" refers to peroxisome proliferator response element; "RPMI" refers to Roswell Park Memorial Institute; "TK" refers to thymidine kinase, "RFU" refers to relative fluorescence unit; and "ESI" refers to electrospray ionization.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Schemes, Preparations, and Examples which follow, including any novel procedures.

Scheme I

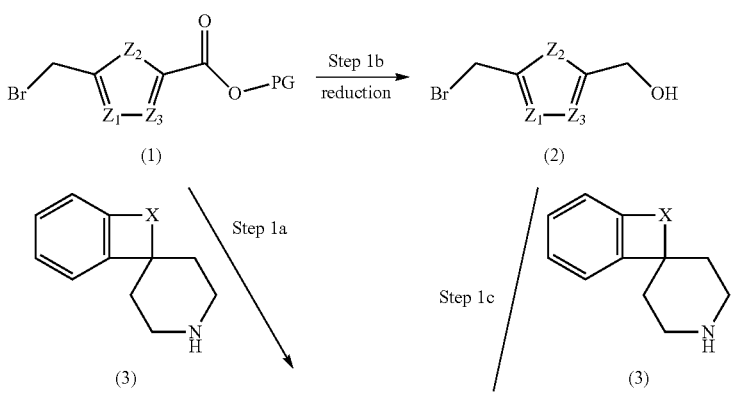

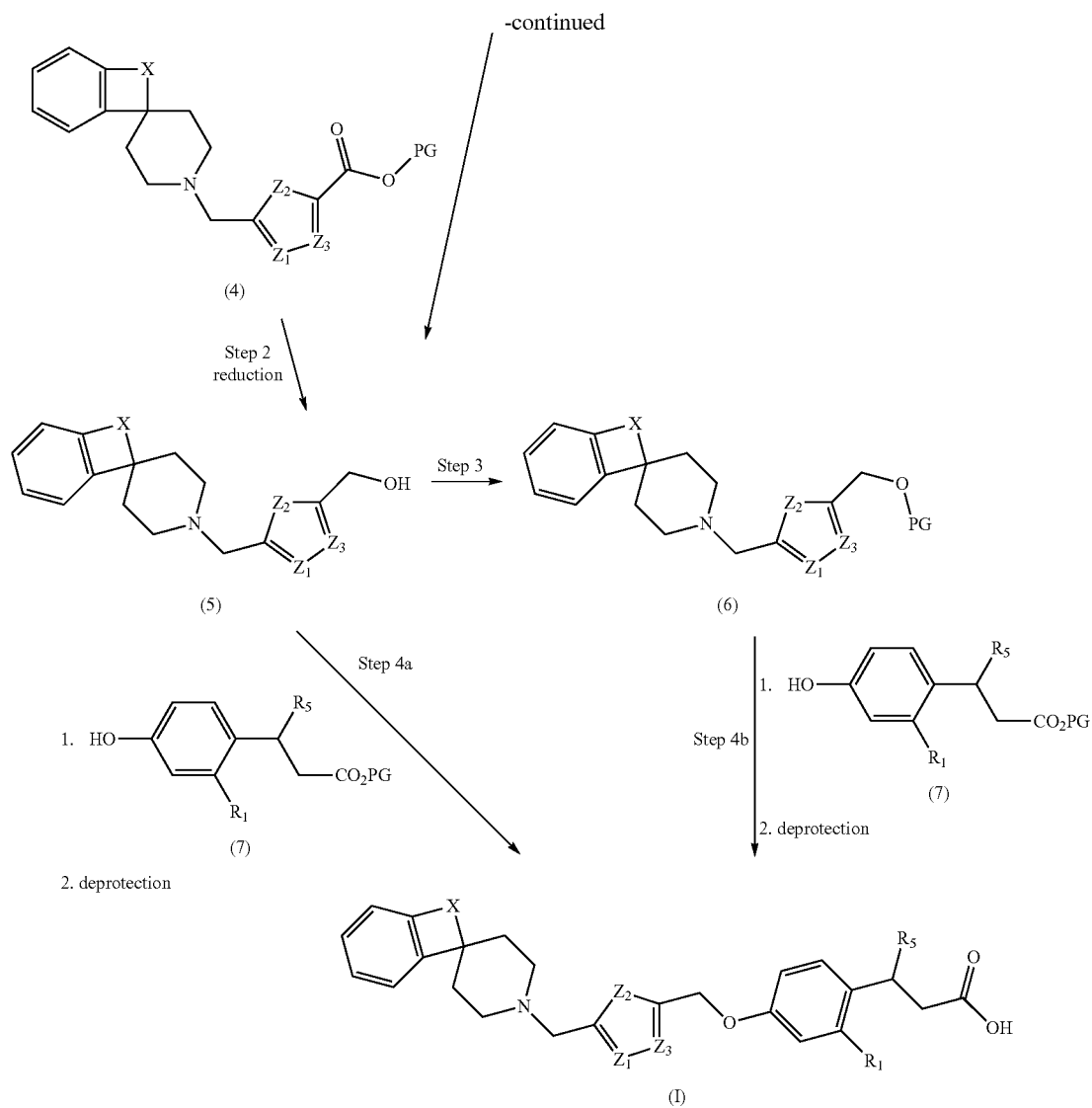

PG = Protecting Group

A compound of Formula I can be prepared in accordance with reactions as depicted in Scheme I. Scheme I (Step 1a) depicts the alkylation of a substituted or unsubstituted aromatic heterocyclic bromomethyl compound (1) with an appropriate substituted piperidine (3) to give, after reduction of the ester in Step 2, a substituted aromatic heterocyclic methyl alcohol (5). Compound (5) can then be further extended through a Mitsunobu reaction at the hydroxyl or alkylation and deprotected to give compounds of Formula I. PG" is a protecting group developed for an acid such as esters and also for an amino group such as carbamates and amides. Such protecting groups are well known and appreciated in the art. See. e.g., Greene and Wuts, *Protective Groups in Organic Synthesis*, supra.

A compound of formula (I) is reacted with a compound of formula (3) under alkylation conditions (Step 1a). One skilled in the art will recognize that there are a number of methods and reagents for amine alkylation resulting from the reaction of heterocyclic bromides and amines. For example, the reaction of an appropriate compound of formula (1) with an appropriate amine or amine salt such as trifluoroacetic acid salt or HCl salt of formula (3) in the presence of a base such as diisopropylethylamine or cesium carbonate will give a compound of formula (4). The ester of formula 4 can be reduced to the alcohol as in Step 2 using a reducing agent such as diisobutylaluminum hydride, lithium aluminum hydride or sodium borohydride to give compound (5). Compound (5) can then be further alkylated with compounds of formula (7) under Mitsunobu conditions and deprotected to give compounds of Formula (I), (Step 4a). Mitsunobu conditions are well known in the art and involve reacting an alcohol (5) with a nucleophile such as a phenol (7) using a phosphine such as tributyl phosphine, triphenyl phosphine, or triethylphosphine and an azodicarbonyl such as ADDP or an azodicarboxylate such as diethyl azodicarboxylate (DEAD). Alternatively, compound 5 can be protected with a protecting group such as methylsulfonyl to give compound (6, Step 3). Compound 6 can then be reacted with (7) using a base such as cesium carbonate and, following deprotection of the acid, give compounds of Formula I. In another variation, a compound of formula (1) can be reduced to a bromomethyl heterocyclic methyl alcohol (2), as shown in Step 1b using a reducing agent such as diisobutyl aluminum hydride or compound (2) may be available commercially and alkylated with an appropriate amine or amine salt of formula (3, Step 1c) in the presence of a base such as diisopropylethylamine or cesium carbonate to give compound (5) and then carried on as described above to give compounds of Formula (I).

In an optional step, a pharmaceutically acceptable salt of a compound of Formula (I) can be formed by reaction of an appropriate acid of Formula (I) with an appropriately pharmaceutically acceptable base in a suitable solvent under standard conditions. Additionally, the formation of such salts can occur simultaneously upon hydrolysis of an ester. The formation of such salts is well known and appreciated in the art.

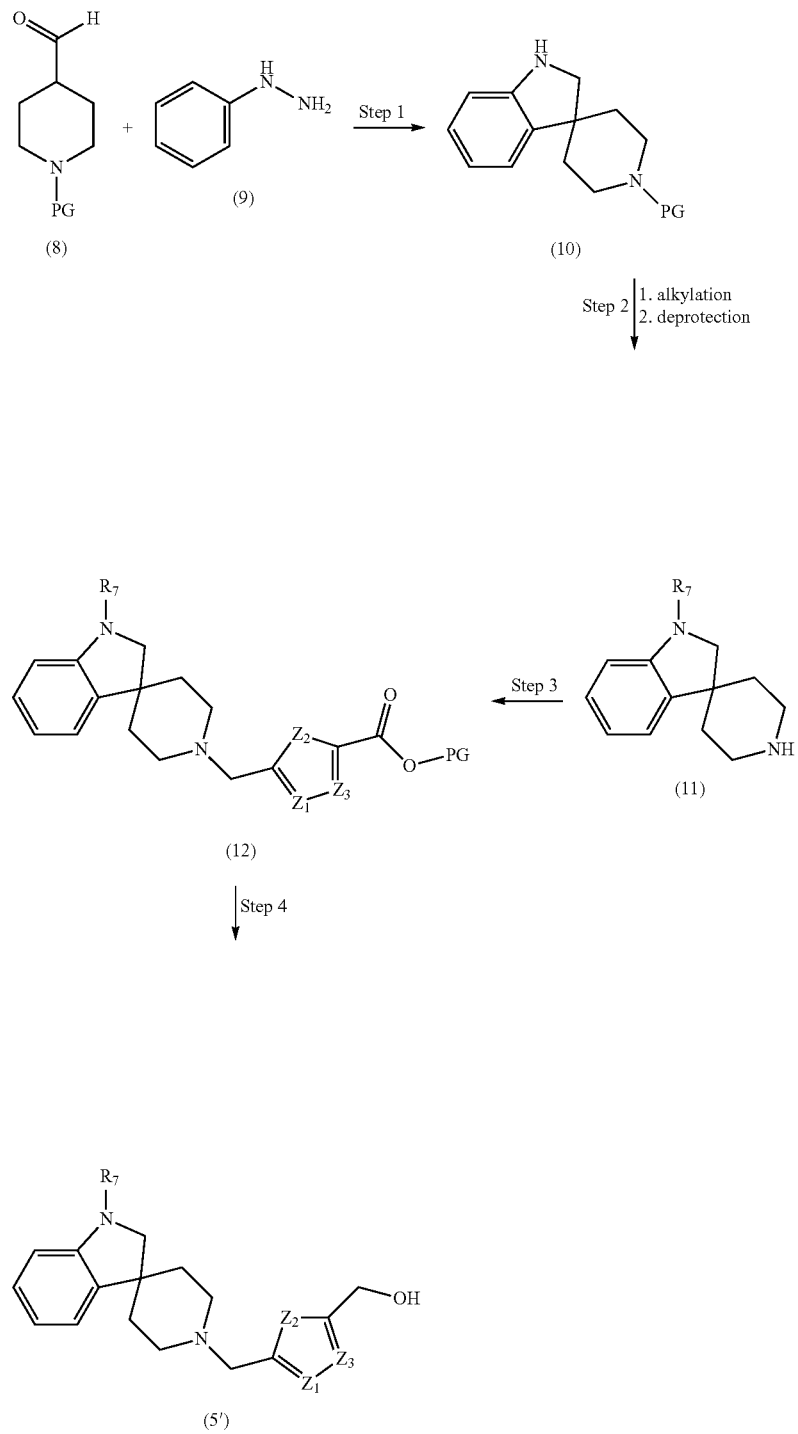

In Scheme II, Step 1, a protected piperidine-4-carboxaldehyde (8) is reacted with a substituted phenylhydrazine (9) in an acid catalyzed cyclization to give a substituted spiro[indoline-3,4'-piperidine] (10) which can then be alkylated to give compounds of Formula (I). For example, to phenyl hydrazine (9) and an appropriate acid such as trifluoroacetic acid is added a nitrogen protected-4-formyl-piperidine (8). After an appropriate reaction time, a reducing agent such as sodium borohydride and an alcohol such as methanol is added to give the desired substituted spiro{indoine-3,4'-protected piperidine] (10). In Step 2, the indoline nitrogen of (10) can be alkylated, for example, by reductive alkylation using an appropriate aldehyde and an appropriate reducing agent such as sodium cyanoborohydride in an appropriate acid such as acetic acid and an alcohol such as methanol. The protecting group on the piperidine nitrogen can be removed under standard conditions well known in the art such as hydrogenation or acidic conditions to give compound (11). Compound (11), in Step 3 can then be alkylated with (1) as previously described in Scheme I, Step 1a, to give compound (12) and reduced in Step 4 as previously described in Scheme I, (steps 1a and 2) to give compound (5'). Compound (5') can then be carried on to give compounds of Formula (I) as described for Scheme I substantially the same as compound (5).

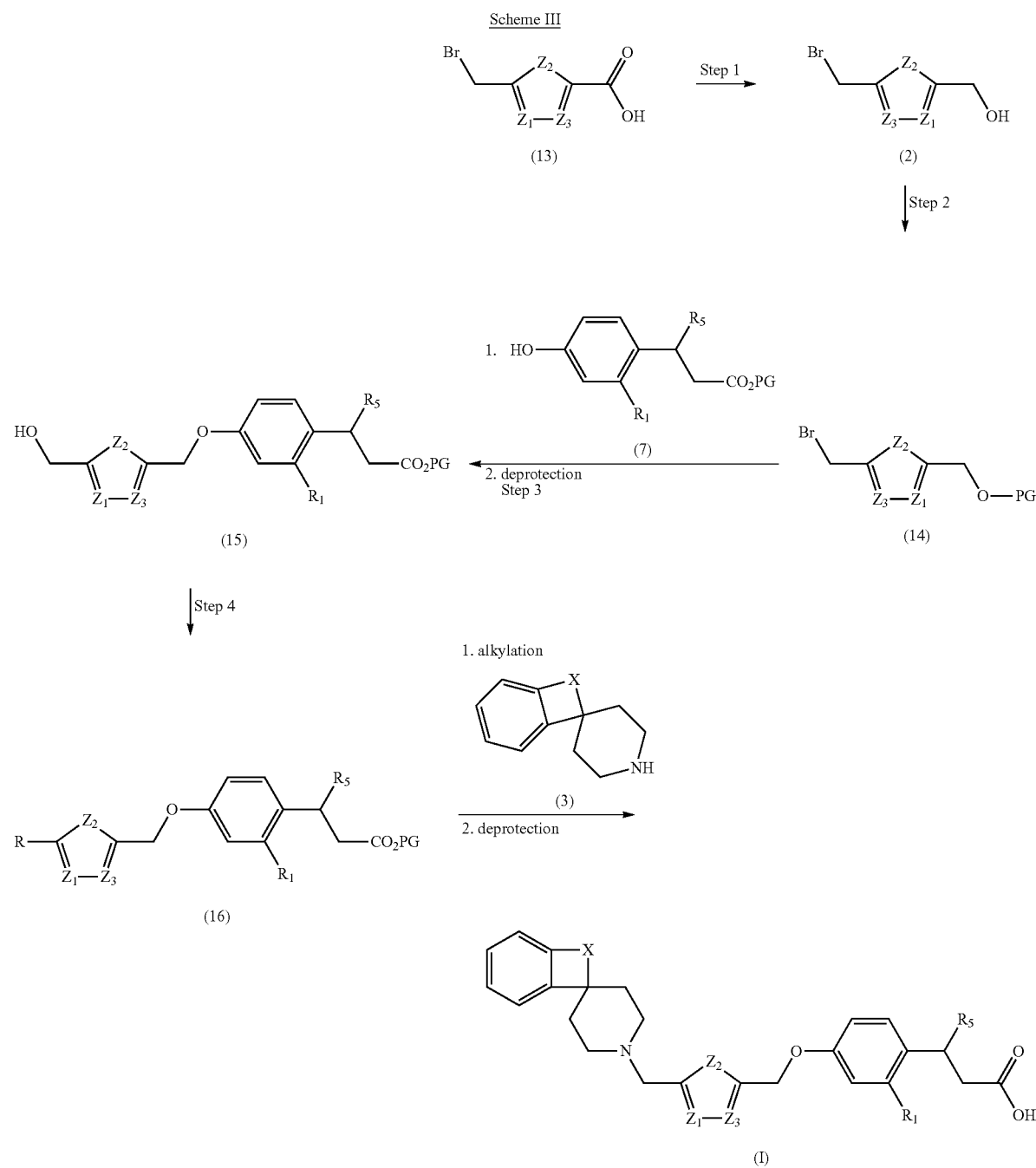

In Scheme III a substituted heterocyclic acid is reduced under conditions well known in the art using a reducing agent such as DIBAL-H to give compound (2) in Step 1. In Step 2, the methyl alcohol, compound (2) can be protected with a protecting group such as tert-butyl-dimethyl silane using a base such as imidazole and tert-butylchlorodimethylsilane to give (14). Compound (14) can be alkylated with compound (7) using a base such as potassium carbonate and deprotected to give compound (15) in Step 3. The methyl alcohol of compound (15) can be converted to an aldehyde with an oxidizing agent such as Dess-Martin periodinane to give compound (16) in Step 4 or to a bromide using brominating conditions such as phosphorus tribromide to give compound (16). Compound (16) can then be alkylated with compound (3), Scheme I, under conditions well known in the art such as reductive alkylation with sodium cyanoborohydride and, followed by deprotection, give compounds of Formula (I). Alternatively a bromide can be alkylated with compound (3) using a base such as cesium carbonate or N,N-diisopropylethylamine and deprotected to give compounds of Formula (I).

PREPARATIONS AND EXAMPLES

The following preparations and examples further illustrate the invention and represent typical synthesis of the compounds of Formula (I). The names for the compounds of the present invention are generally provided by IUPAC-NAMET™, ACDLABS™ or Symyx Draw 3.2.

Preparation 1

Benzyl spiro[indoline-3,4'-piperidine]-1'-carboxylate

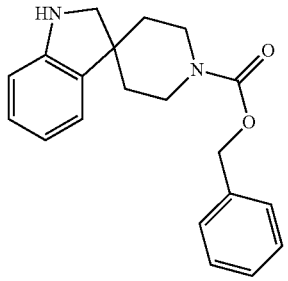 [SMILES: O=C(OCc1ccccc1)N1CCC2(CC1)CNc1ccccc12]

A solution of phenyl hydrazine (1.29 g, 12.0 mmol) and trifluoroacetic acid (3.0 mL) in a 49/1 solution of toluene/acetonitrile (50 mL) is heated at 35° C. 4-Formyl-piperidine-1-carboxylic acid benzyl ester (2.7 g, 10.91 mmol) is dissolved in a 49/1 solution of toluene/acetonitrile (10 mL) and added dropwise to the mixture (WO2005046682). The mixture is stirred at 35° C. overnight. The resulting solution is cooled to 0° C., and methanol (5 mL) is added. NaBH$_4$ (0.619 g, 16.38 mmol) is added slowly to the solution and the mixture is stirred for 45 min. The mixture is washed with aqueous NH$_4$OH (6%, 25 mL) and brine (30 mL), dried over sodium sulfate, and evaporated to dryness to give a yellow solid. The crude solid is recrystallised from EtOAc to give a pale yellow solid (1.25 g, 1$^{st}$ crop). The mother liquor is evaporated and purified by flash chromatography, eluting with hexane:ethyl acetate (8:2) to give the title compound as a pale yellow solid (1.2 g, 2$^{nd}$ crop) with a total yield (2.4 g, 84%). ESI/MS m/z 323 (M+H)$^+$.

Preparation 2

Benzyl 1-methylspiro[indoline-3,4'-piperidine]-1'-carboxylate

To a 0° C. solution of benzyl 1,2-dihydro-1'H-spiro[indole-3,4'-piperidine]-1'-carboxylate (315 g, 977.5 mmol), formaldehyde (40% aqueous solution, 138 mL, 4.9 mol) and acetic acid (279 mL, 4.9 mol) in methanol (6.0 L), is added sodium cyanoborohydride (184 g, 2.9 mol) in portions over a period of 2 h (some effervescence is observed). The reaction mixture is allowed warm to room temperature and stirred for 6 h. The pH of the mixture is adjusted to about 8 with 10% NaHCO$_3$ solution and extracted with EtOAc (3×5.0 L). The combined extracts are washed with water (2×2.5 L) and brine (2.5 L), dried over sodium sulfate, and evaporated to dryness to give the title compound as a pale yellow solid (310 g, 98.3%). ESI/MS m/z 337 (M+H)$^+$.

Preparation 3

1-Methylspiro[indoline-3,4'-piperidine]

To a solution of benzyl 1-methylspiro[indoleine-3,4'-piperidine]-1'-carboxylate (0.85 g, 2.52 mmol) in methanol (50 mL) is added Pd(OH)$_2$/C (10%, 0.15 g) and the mixture is hydrogenated with a balloon for 16 hours. The reaction mixture is filtered through diatomaceous earth, washed with methanol (50 mL), and evaporated to dryness to give the title compound (0.5 g, 98%). ESI/MS m/z 203.4 (M+H)$^+$.

Preparation 4

(3S)-3-(4-Hydroxyphenyl)hex-4-ynoic acid

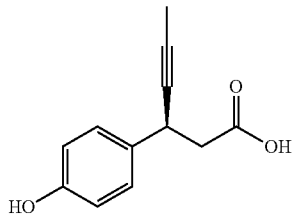

3-(4-Hydroxyphenyl)hex-4-ynoic acid enantiomers are separated by chiral chromatography [column chiralpak IA (250 mm×4.6 mm), mobile phase (A) n-hexane, mobile phase (B) isopropyl alcohol with 0.01% TFA; composition (85:15), flow rate 1.0 mL/min, detection 225 nm) to give the title compound (4.2 g, 50.58%) retention time 7.96. ESI/MS m/z 203 (M+H)$^-$. The mixture of enantiomers is also separated by chiral resolution using a similar method as described in WO2005086661 to give the title compound.

Preparation 5

Methyl 5-(bromomethyl)-4-methyl-thiophene-2-carboxylate

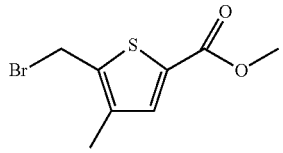

To a solution of methyl 4-methylthiophene-2-carboxylate (2.7 g, 6.4 mmol) in dichloromethane (20 mL) is added 48% aq. HBr (12 mL), H$_2$SO$_4$ (6 mL), ZnBr$_2$ (5.4 g), and HCHO (2.2 mL, 37%) at 0-5° C. The mixture is stirred at room temperature for 16 hours. The solution is diluted with water, extracted with dichloromethane, washed with NaHCO$_3$ solution, saturated brine solution, water, dried over sodium sulfate, and concentrated to give the title compound as an off white solid (3.5 g, 81%).

Preparation 6

Ethyl 2-(2-hydroxypropylamino)-2-oxo-acetate

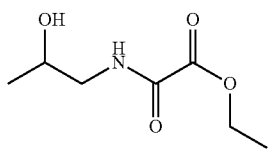

To a stirred solution of 1-amino-propan-2-ol (15.0 g, 199.7 mmol) in DCM (150.0 mL), is added triethylamine (43.30 mL, 299.56 mmol) at 0° C. Chloro-oxo-acetic acid ethyl ester (22.35 mL, 199.7 mmol) is added dropwise to the reaction mixture at 0° C. and the reaction mixture is stirred for 16 hours at room temperature. The mixture is diluted with water (100 mL) at 0° C., extracted with DCM (2×100 mL), washed with water (2×50 mL) and brine (50 mL), dried over $Na_2SO_4$, and evaporated to dryness. The crude product is purified by silica gel chromatography, eluting with hexane:ethyl acetate (3.0:7.0) to give the title compound as a pale yellow gel (10.7 g, 31.0%). ESI/MS m/z 176.2 $(M+H)^+$.

Preparation 7

Ethyl 2-(acetonylamino)-2-oxo-acetate

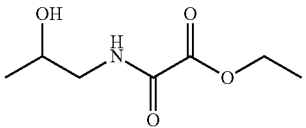

To a stirred solution of ethyl 2-(2-hydroxypropylamino)-2-oxo-acetate (10.7 g, 61.07 mmol) in DCM (100.0 mL), is added Dess Martin periodinane (25.9 g, 61.07 mmol) at 0° C. The reaction mixture is stirred at room temperature for 2 hours, diluted with water (100 mL) at 0° C., and extracted with DCM (2×100 mL). The combined organic layer is washed with water (2×50 mL) and saturated brine (50 mL), dried over $Na_2SO_4$, and evaporated under reduced pressure. The crude material is purified by silica gel chromatography, eluting with hexane:ethyl acetate (1:1) to give the title compound as a light yellow oil (9.2 g, 87.03%). ESI/MS m/z 174.1 $(M+H)^+$.

Preparation 8

Ethyl 5-methyloxazole-2-carboxylate

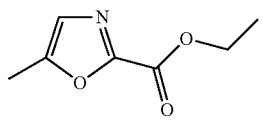

To a stirred solution of ethyl 2-(acetonylamino)-2-oxo-acetate (9.2 g, 53.12 mmol) in toluene (100.0 mL), is added $POCl_3$ (4.95 mL, 53.12 mmol) and the reaction mixture is refluxed for 16 hours. The reaction mixture is cooled, added portionwise to water (100.0 mL) and stirred vigorously. The organic layer is washed with saturated $NaHCO_3$ solution (2×50 mL), water (2×50 mL), dried over $Na_2SO_4$, and evaporated under reduced pressure. The crude material is purified by silica gel chromatography eluting with hexane:ethyl acetate (8.0:2.0) to give the title compound (5.1 g, 61.9%) as a yellow oil. ESI/MS m/z 156.2.1 $(M+H)^+$.

Preparation 9

Ethyl 5-(bromomethyl)oxazole-2-carboxylate

To a stirred solution of ethyl 5-methyloxazole-2-carboxylate (5.1 g, 32.87 mmol) and NBS (8.19 g, 46.02 mmol) in carbon tetrachloride (50.0 mL), is added benzoyl peroxide (0.79 g, 3.29 mmol) and the reaction mixture is refluxed for 16 hours. The mixture is cooled to room temperature and filtered through diatomaceous earth. The filtrate is concentrated in vacuum and the crude is purified by silica gel chromatography, eluting with hexane:ethyl acetate (9.2:0.8) to give (4.8 g, 62.33%) of the title compound as a light brown oil. ESI/MS m/z ($^{79}Br/^{81}Br$) 234.1/236.1 $[M+H]^+$.

Preparation 10

Methyl 3-methoxythiophene-2-carboxylate

To a mixture of 3-hydroxy-thiophene-2-carboxylic acid methyl ester (5 g, 31.6 mmol) and $K_2CO_3$ (22.2 g, 161 mmol) in acetone (50 mL) is added $CH_3I$ (10.8 mL, 173 mmol,) dropwise at 0° C. The reaction mixture is heated at 55° C. for 4 hours, cooled to room temperature, filtered through diatomaceous earth, and the filtrate is concentrated under vacuum. The residue is diluted with water (100 mL) and extracted with ethyl acetate (2×200 mL). The combined organic layer is washed with brine solution (50 mL), dried over $Na_2SO_4$, and evaporated under vacuum to give title compound as a brown solid (5.9 g). ESI/MS m/z 173.1 $(M+H)^+$.

Preparation 11

Methyl 5-(bromomethyl)-3-methoxy-thiophene-2-carboxylate

To a solution of 3-methoxy-thiophene-2-carboxylic acid methyl ester (5 g, 29 mmol) in anhydrous dichloromethane (50 mL), aqueous HBr (22 mL, 37%), 98% $H_2SO_4$ (11 mL), $ZnBr_2$ (8.5 g) and aqueous formaldehyde (37%, 3.8 mL) are sequentially added at 0° C. The reaction mixture is stirred at room temperature for 14 h. The organic layer is separated and the aqueous layer is extracted with DCM (2×200 m L). The combined organic layers are washed with brine solution (200 mL), dried over $Na_2SO_4$, and evaporated under vacuum. The crude material is purified by silica gel chromatography eluting with hexane:ethyl acetate (9.5:0.5) to give title compound (4.4 g, 60%). ESI/MS m/z 267.1 $(M+H)^+$.

Preparation 12

(5-Bromomethyl-3-methoxy-thiophen-2-yl)-methanol

To a solution of 5-bromomethyl-3-methoxy-thiophene-2-carboxylic acid methyl ester (1.4 g, 5.2 mmol) in anhydrous dichloromethane (50 mL) is added diisobutyl aluminum hydride (1M in hexane, 21.0 mL, 21.1 mmol) dropwise at −78° C. After the completion of the addition, the mixture is warmed to room temperature and stirred for 2 hours. The reaction mixture is quenched with water (15 mL) at −40° C. and the mixture is agitated for 30 minutes at room temperature. The reaction mixture is filtered through diatomaceous earth. The filtrate is dried over sodium sulfate and concentrated, to give the title compound as a pale yellow liquid (1.2 g, 96%). $^1$H NMR (400 MHz, d$_6$ DMSO) 7.46 (s, 1H), 4.58 (s, 2H), 3.84 (s, 3H), 3.73 (s, 2H).

Preparation 13

[5-(Bromomethyl)-3-methoxy-2-thienyl]methoxy-tert-butyl-dimethyl-silane

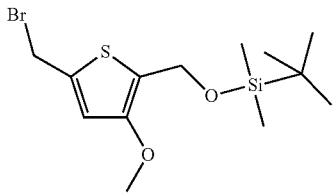 [SMILES: COc1cc(CBr)sc1CO[Si](C)(C)C(C)(C)C]

To a solution of (5-bromomethyl-3-methoxy-thiophen-2-yl)-methanol (0.6 g, 2.5 mmol) in anhydrous dichloromethane (10 mL) is added imidazole (0.516 g, 7.59 mmol) and tert-butylchlorodimethylsilane (0.412 g, 2.75 mmol) at 0° C. The reaction mixture is allowed to warm to room temperature and stirred for 1 hour. The reaction mixture is quenched with water and concentrated. The residue is dissolved in DCM, washed with water (25 mL) and brine (25 mL), dried over Na$_2$SO$_4$, filtered, and concentrated to give the title compound (0.9 g). ESI/MS m/z ($^{79}$Br/$^{81}$Br) 351/353.1 [M+H]$^+$.

Preparation 14

Ethyl 3-[4-[[5-[(tert-butyl(dimethyl)silyl)oxymethyl]-4-methoxy-2-thienyl]methoxy]-2-fluoro-phenyl]propanoate

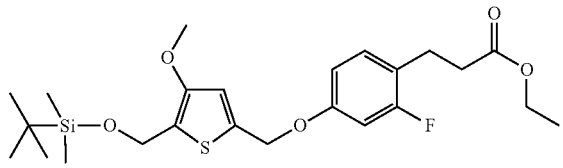 [SMILES: CCOC(=O)CCc1ccc(OCc2cc(OC)c(CO[Si](C)(C)C(C)(C)C)s2)cc1F]

To a solution of 3-(2-fluoro-4-hydroxy-phenyl)-propionic acid ethyl ester (1.03 g, 4.8 mmol) in acetonitrile (15 mL) is added potassium carbonate (2.31 g, 16.8 mmol) and (5-bromomethyl-3-methoxy-thiophen-2-ylmethoxy)-tert-butyl-dimethyl-silane (1.7 g, 4.8 mmol) at room temperature and the reaction mixture is refluxed for 3 hours. The reaction mixture is concentrated, diluted with water, and extracted with EtOAc (2×30 mL). The combined extracts are washed with water (15 mL) and saturated brine (15 mL), dried over Na$_2$SO$_4$, filtered, and concentrated. The crude material is purified by silica gel chromatography eluting with hexane: ethyl acetate (9.6:0.4) to give the title compound (0.5 g, 21%). $^1$H NMR (400 MHz, DMSO d$_6$) δ 7.51 (s, 1H), 7.26-7.2 (t, J=8.4 Hz, 1H), 6.92-6.89 (d, J=12 Hz, 1H), 6.83-6.81 (d, J=7.6 Hz, 2H), 4.92 (s, 2H), 4.82 (s, 2H), 4.10-4.05 (q, J=6.4 Hz, 2H), 3.82 (s, 3H), 2.86-2.82 (t, J=16 Hz, 2H), 2.61-2.55 (m, 2H), 1.21-1.17 (t, J=6.8 Hz, 3H), 0.89 (s, 9H), 0.13 (s, 6H).

Preparation 15

Ethyl 3-[2-fluoro-4-[[5-(hydroxymethyl)-4-methoxy-2-thienyl]methoxy]phenyl]propanoate To a solution of 3-{4-[5-(tert-butyl-dimethyl-silanyloxymethyl)-4-methoxy-thiophen-2-ylmethoxy]-2-fluoro-phenyl}-propionicacid ethyl ester (0.5 g, 1.0 mmol) in THF (5 mL) is added tetra-n-butylammoniumfluoride (1M solution in THF, 2 mL, 2.0 mmol) at 0° C. and the reaction mixture is stirred for 30 minutes at 25° C. The reaction mixture is quenched with water and evaporated to a residue. The residue is extracted with EtOAc, washed with water (15 mL) and brine (15 mL), dried over sodium sulfate, filtered, and concentrated to give the title compound (0.4 g,). $^1$H NMR (400 MHz, DMSO d$_6$) δ7.41 (s, 1H), 7.19-7.15 (t, J=8.8 Hz, 1H), 6.85-6.75 (m, 2H), 5.32 (br, 1H), 4.85 (s, 2H), 4.55 (s, 2H), 4.04-4.00 (q, J=7.2 Hz, 2H), 3.75 (s, 3H), 3.58 (s, 1H) 3.16-3.12 (t, J=15.2 Hz, 3H), 2.79-2.76 (t, J=14.8 Hz, 2H), 2.55-2.51 (t, J=15.2 Hz, 2H), 1.28-1.22 (t, J=7.2 Hz, 3H), Preparation 16

Ethyl 3-[2-fluoro-4-[(5-formyl-4-methoxy-2-thienyl)methoxy]phenyl]propanoate

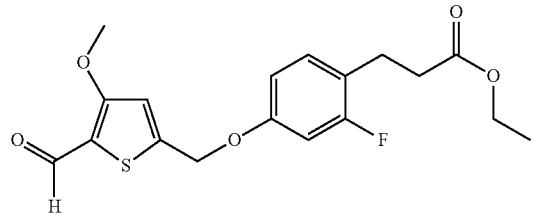 [SMILES: CCOC(=O)CCc1ccc(OCc2cc(OC)c(C=O)s2)cc1F]

To a solution of ethyl 3-[2-fluoro-4-[[5-(hydroxymethyl)-4-methoxy-2-thienyl]methoxy]phenyl]propanoate (1.6 g, 4.3 mmol) in anhydrous dichloromethane (10 mL), cooled to 0° C., is added Dess-Martin periodinane (2.76 g, 6.5 mmol). The reaction mixture is warmed to room temperature and stirred for 2 hours. The reaction mixture is diluted with water (15 mL), extracted with ethyl acetate, washed with water (15 mL), brine (15 mL), dried over sodium sulfate, filtered, and evaporated to dryness. The crude material is purified by silica gel chromatography eluting with hexane:ethyl acetate (8.8:1.2) to give the title compound (0.8 g, 50%). ESI/MS m/z 367.1 (M+H)$^+$.

Preparation 17

Ethyl 5-(spiro[indene-1,4'-piperidine]-1'-ylmethyl)thiophene-2-carboxylate

Method A

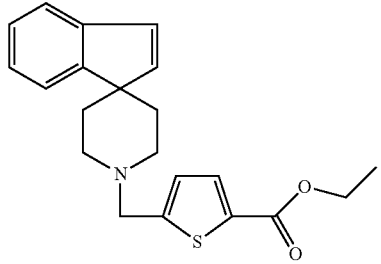 [SMILES: CCOC(=O)c1ccc(CN2CCC3(C=Cc4ccccc43)CC2)s1]

To a solution of spiro[indene-1,4'-piperidine] (1.4 g, 6.3 mmol) in ethanol (28 mL) is added methyl 5-(bromomethyl)thiophene-2-carboxylate (1.78 g, 7.6 mmol) and diisopropylamine (3.31 mL, 19 mmol) at room temperature and the reaction mixture is stirred for 16 hours at 90° C. The mixture is concentrated, diluted with water, and extracted with ethyl acetate (2×200 mL). The combined extracts are washed with water (50 mL) and saturated brine (50 mL), dried over sodium sulfate, filtered, and concentrated to give the title compound (1.5 g, 58%). ESI/MS m/z 340.1 (M+H)$^+$.

Method B

Spiro[indene-1,4'-piperidine]hydrochloride (128.0 g, 560 mmol) is dissolved in ethanol (1.5 L) under a nitrogen atmosphere at 30° C. Diisopropylethylamine (407.4 mL, 1.68 mol) is added dropwise at 30° C. over a period of 10 minutes, and is stirred for 20 minutes. Methyl 5-(bromomethyl)thiophene-2-carboxylate (~50% pure by LCMS) (300 g, 1.27 mol) is added at 30° C. and stirred at 30° C. for 10 minutes and the mixture is heated to 60° C. for 1 h 45 min. The reaction is monitored by TLC showed the presence of starting material. The reaction is stirred for 13 hours at 30° C. The reaction mixture is concentrated and dissolved in DCM (10 L). HCl (1N, 1.5 L) is added dropwise with constant stirring and a white solid precipitates and is collected. The material is dissolved in DCM (1 L), stirred for 10 minutes, filtered, and dried under vacuum (44° C.) to give the title compound (150.0 g, 76%). ESI/MS m/z 340.1 (M+H)$^+$.

The following compounds are prepared essentially as described by the method of preparation 17 (Method A).

| Prep. No. | Chemical Name | ESI/MS (m/z) (M + H) |
|---|---|---|
| 18 | Ethyl 5-(1'H-spiro[indene-1,4'-piperidin]-1'-ylmethyl)-1,3-oxazole-2-carboxylate | 500 |
| 19 | 2-Bromo-4-methyl-5-(spiro[indene-1,4'-piperidine]-1'-ylmethyl)thiazole | a |
| 20 | Ethyl 2-[(1-methylspiro[indoline-3,4'-piperidine]-1'-yl)methyl]thiazole-5-carboxylate | 372 |
| 21 | Ethyl 5-[(1-methylspiro[indoline-3,4'-piperidine]-1'-yl)methyl]thiophene-2-carboxylate | 357 |
| 22 | Methyl 4-methyl-5-(spiro[indane-1,4'-piperidine]-1'-ylmethyl)thiophene-2-carboxylate | b |
| 23 | Methyl 5-(spiro[indane-1,4'-piperidine]-1'-ylmethyl)thiophene-2-carboxylate | 342 |
| 24 | Methyl 5-(spiro[indene-1,4'-piperidine]-1'-ylmethyl)furan-2-carboxylate | 324 |
| 25 | Ethyl 5-(spiro[indene-1,4'-piperidine]-1'--methyl-thiazole-2-carboxylate | 355 |
| 26 | Ethyl 5-(spiro[indane-1,4'-piperidine]-1'-ylmethyl)oxazole-2-carboxylate | 341 |
| 27 | Methyl 5-[(1-methylspiro[indoline-3,4'-piperidine]-1'-yl)methyl]furan-2-carboxylate | 341 | a. Crude product
b. $^1$H NMR (400 MHz, DMSO-d$_6$): δ 7.53 (s, 0.5H), 7.21-7.12 (m, 2H), 3.76 (s, 1.5H), 3.65 (s, 1H), 2.84-2.82 (d, J = 8 Hz, 2H), 2.26-2.21 (t, J = 8 Hz, 1H), 2.16 (s, 1.5H), 1.96-1.92 (d, J = 8 Hz, 1H), 1.79 (s, 1H), 1.45-1.42 (m, 1H).

Preparation 28

[5-(Spiro[indene-1,4'-piperidine]-1'-ylmethyl)-2-thienyl]methanol

Method A

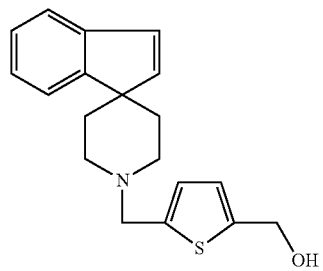 [SMILES: OCc1ccc(CN2CCC3(C=Cc4ccccc43)CC2)s1]

To a solution of ethyl 5-(spiro[indene-1,4'-piperidine]-1'-ylmethyl)thiophene-2-carboxylate (1.5 g, 4.4 mmol) in dichloromethane (30 mL) is added DIBAL-H (11 mL, 11.06 mmol) at −78° C. The reaction mixture is allowed to warm to room temperature for 1 hour followed by the dropwise addition of water at 0° C. The mixture is filtered through diatomaceous earth, extracted with dichloromethane, and evaporated to dryness to give the title compound (1.05 g, 76%). ESI/CMS m/z 312.1 (M+H)$^+$.

Method B

Methyl 5-(spiro[indene-1,4'-piperidine]-1'-ylmethyl)thiophene-2-carboxylate (150.0 g, 446.0 mmol) is dissolved in anhydrous dichloromethane (3 L) under a nitrogen atmosphere at 30° C. The mixture is cooled to −78° C. and DIBAL-H (1.0 M solution in toluene) (1.2 L, 960 mmol) is added dropwise at −78° C. under a nitrogen atmosphere over a period of 1 hour with constant stirring. The reaction mixture is gradually warmed to 0° C. and stirred for 3 h at 0° C. and 3 h at 30° C. The mixture is cooled to −78° C. and saturated aqueous NH$_4$OH solution (1 L) is added dropwise followed by the dropwise addition of DCM (5.0 L). The mixture is warmed to room temperature and extracted with DCM, washed with water (2 L) and saturated brine (2 L), dried over sodium sulfate, and evaporated to dryness. To the residue is added diethyl ether (500 mL) and the mixture is stirred for 30 min. The precipitate that is formed is filtered, the filtrate evaporated to dryness and combined with the solid to give the title compound as a white solid (88.0 g, 64%). ESI/MS m/z 312.1 (M+H)$^+$.

The following compounds are prepared essentially as described by the method of preparation 28 (Method A)

| Prep. No. | Chemical Name | ESI/MS (m/z) (M + H) |
|---|---|---|
| 29 | [5-[(1-Methylspiro[indoline-3,4'-piperidine]-1'-yl)methyl]-2-furyl]methanol | 313 |
| 30 | [5-(Spiro[indane-1,4'-piperidine]-1'-ylmethyl)oxazol-2-yl]methanol | 299 |
| 31 | [2-(Spiro[indene-1,4'-piperidine]-1'-ylmethyl)thiazol-5-yl]methanol | 313 |
| 32 | [2-(Spiro[indane-1,4'-piperidine]-1'-ylmethyl)thiazol-5-yl]methanol | 315 |
| 33 | [2-[(1-Methylspiro[indoline-3,4'-piperidine]-1'-yl)methyl]thiazol-5-yl]methanol | 330 |
| 34 | [5-[(1-Methylspiro[indoline-3,4'-piperidine]-1'-yl)methyl]-2-thienyl]methanol | 329 |
| 35 | [4-Methyl-5-(spiro[indane-1,4'-piperidine]-1'-ylmethyl)-2-thienyl]methanol | 328 |
| 36 | [5-(Spiro[indane-1,4'-piperidine]-1'-ylmethyl)-2-thienyl]methanol | 314 |
| 37 | [5-(Spiro[indene-1,4'-piperidine]-1'-ylmethyl)-2-furyl]methanol | 296 |
| 38 | [5-(Spiro[indene-1,4'-piperidine]-1'-ylmethyl)oxazol-2-yl]methanol | 297 |

Preparation 39

4-Methyl-5-(spiro[indene-1,4'-piperidine]-1'-ylmethyl)thiazole-2-carbaldehyde

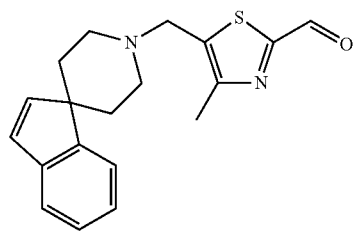 [SMILES: Cc1nc(C=O)sc1CN1CCC2(C=Cc3ccccc32)CC1]

To a solution of 2-bromo-4-methyl-5-(spiro[indene-1,4'-piperidine]-1'-ylmethyl) thiazole (3.8 g, 10.12 mmol) in THF is added n-BuLi (0.713 g, 11.13 mmol) at −78° C. The mixture is warmed to −45° C. and stirred for 30 minutes. DMF (1.5 mL) is added dropwise to the mixture at −78° C. and the mixture is slowly warmed to room temperature and stirred for an hour. The mixture is cooled to −78° C., diluted with water, followed by NH$_4$Cl solution. The mixture is extracted with ethyl acetate, dried over Na$_2$SO$_4$, and evaporated to dryness to give the title compound (2.8 g, 85%). ESI/MS m/z 325 (M+H)$^+$.

The following compound is prepared essentially as described by the method of preparation 39

| Prep. No. | Chemical Name | ESI/MS (m/z) (M + H) |
|---|---|---|
| 40 | 5-(Spiro[indene-1,4'-piperidine]-1'-ylmethyl)thiazole-2-carbaldehyde | 311 |

Preparation 41

5-(Spiro[inden-1,4'-piperidine]-'ylmethyl)-4-methyl-thiazole-2-methanol

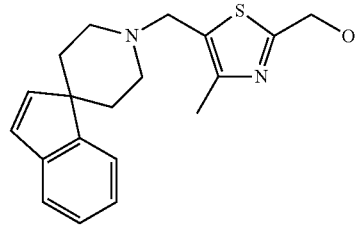 [SMILES: Cc1nc(CO)sc1CN1CCC2(C=Cc3ccccc32)CC1]

To a solution of 4-methyl-5-(spiro[indene-1,4'-piperidine]-1'-ylmethyl)thiazole-2-carbaldehyde (0.600 g, 1.8 mmol) in DCM (6 mL) is added DIBAL-H (1M solution in hexane, 0.52 g, 3.6 mL, 3.6 mmol) at −78° C. and the mixture is warmed to room temperature and stirred for 1 hour. The mixture is cooled to −78° C., quenched with water, filtered, extracted with DCM, and evaporated to dryness to give the title compound (0.500 g, 83%). ESI/MS m/z 327 (M+H)$^+$.

The following compound is prepared essentially as described by the method of preparation 41

| Prep. No. | Chemical Name | ESI/MS (m/z) (M + H) |
|---|---|---|
| 42 | [5-(Spiro[indene-1,4'-piperidine]-1'-ylmethyl)thiazol-2-yl]methanol | 313 |

Preparation 43

[5-(Spiro[indene-1,4'-piperidine]-1'-ylmethyl)oxazol-2-yl]methyl methanesulfonate

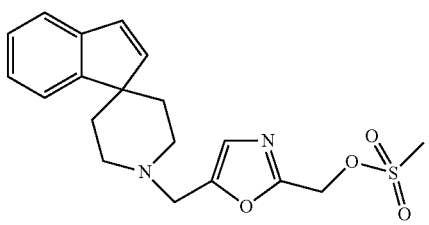 [SMILES: CS(=O)(=O)OCc1ncc(CN2CCC3(C=Cc4ccccc43)CC2)o1]

To a 0° C. stirred solution of [5-(spiro[indene-1,4'-piperidine]-1'-ylmethyl)oxazol-2-yl]methanol (0.15 g, 0.51 mmol) in DCM (10.0 mL) is added triethylamine (0.18 mL, 1.26 mmol) and methane sulphonyl chloride (0.05 mL, 0.61 mmol). The reaction mixture is stirred at 0° C. for 1 hour. The reaction mixture is washed with water (20.0 mL) and brine (10.0 mL), extracted with DCM, dried over $Na_2SO_4$, and evaporated to dryness to give the crude product (0.18 g) as a brown liquid.

The following compound is prepared essentially as described by the method of preparation 43

| Prep. No. | Chemical Name | ESI/MS (m/z) (M + H) |
|---|---|---|
| 44 | [5-(spiro[indane-1,4'-piperidine]-1'-ylmethyl)oxazol-2-yl]methyl methanesulfonate | 377 |

Preparation 45

Ethyl (3S)-3-[4-[[5-(spiro[indene-1,4'-piperidine]-1'-ylmethyl)-2-thienyl]methoxy]phenyl]hex-4-ynoate Method A

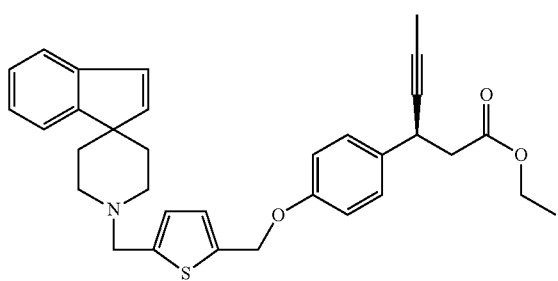 [SMILES: CC#C[C@@H](CC(=O)OCC)c1ccc(OCc2ccc(CN3CCC4(C=Cc5ccccc54)CC3)s2)cc1]

To a solution of 1,1'-(azodicarbonyl)dipiperidine (1.30 g, 5.1 mmol) in THF (5 mL) is added tributylphosphine (1.21 g, 6.0 mmol) at 0° C. After 15 minutes at 0° C., a solution of [5-(spiro[indene-1,4'-piperidine]-1'-ylmethyl)-2-thienyl]methanol (0.8 g, 3.4 mmol) in THF (5 mL) is added and the reaction mixture is stirred for 15 minutes at 0° C. followed by the addition of ethyl (3S)-3-(4-hydroxyphenyl)hex-4-ynoate (1.07 g, 3.4 mmol) in THF (5 mL). The reaction mixture is stirred for 16 hours at room temperature, filtered, diluted with water, and extracted with ethyl acetate (2×200 mL). The combined extracts are washed with water (50 mL) and brine (50 mL), dried over sodium sulfate, filtered, and concentrated. The crude product is purified by silica gel chromatography eluting with hexane:ethyl acetate (8.5:1.5) to give the title compound (1.1 g, 61%). ESI/MS m/z 526.2 (M+H)$^+$.

Method B

Ethyl (3S)-3-(4-hydroxyphenyl)hex-4-ynoate (30.0 g, 129.0 mmol) is dissolved in THF (600 ml) under a nitrogen atmosphere and cooled to 0° C. DIAD (31.3 g. 154.9 mol) is added slowly at 0° C. and stirred the mixture stirred for 30 min A solution of $PPh_3$ (40.65 g, 154.9 mmol) and (5-[5-(spiro[indene-1,4'-piperidine]-1'-ylmethyl)-2-thienyl]methanol (48.26 g, 154.9 mmol), dissolved in a minimum amount of THF, is added to the reaction mixture at 0° C. and the mixture is warmed to room temperature and stirred for 12 hours. The solvent is evaporated and the residue is dissolved in ethyl acetate (300 mL), washed with water (2×10 volumes) and brine (10 volumes), dried over $Na_2SO_4$, and evaporated to dryness. The crude material is purified by silica gel chromatography, eluting with hexane:ethyl acetate (9.0:1.0) to give the title compound (33.0 g, 48.6%). $^1$H NMR (DMSO-d$_6$) δ 7.44-7.42 (d, 1H), 7.32-7.27 (m, 2H), 7.22-7.12 (m, 2H), 7.03-7.02 (d, 1H), 6.97-6.92 (m, 3H), 6.89-6.88 (d, 1H), 6.79-677 (d, 1H), 6.69-6.67 (d, 1H), 5.21 (s, 2H), 4.02-4.01 (m, 1H), 3.77 (s, 2H), 2.94-2.91 (d, 2H), 2.68-2.62 (m, 3H), 2.41-2.36 (m, 2H), 2.10-2.03 (m, 2H), 1.77 (s, 3H), 1.39 (s, 1H), 1.27-1.14 (m, 4H), 1.13-1.11 (t, 3H).

The following compounds are prepared essentially as described by the method of preparation 45 (Method A)

| Prep. No. | Chemical Name | ESI/MS (m/z) (M + H) |
|---|---|---|
| 46 | Ethyl (3S)-3-[4-[[5-[(1-methylspiro[indoline-3,4'-piperidine]-1'-yl)methyl]-2-furyl]methoxy]phenyl]hex-4-ynoate | 527 |
| 47 | Ethyl 3-[2-fluoro-4-[[5-(spiro[indene-1,4'-piperidine]-1'-ylmethyl)-2-furyl]methoxy]phenyl]propanoate | 490 |
| 48 | Ethyl (3S)-3-[4-[[2-(spiro[indane-1,4'-piperidine]-1'-ylmethyl)thiazol-5-yl]methoxy]phenyl]hex-4-ynoate | 529 |
| 49 | Ethyl (3S)-3-[4-[[4-methyl-5-(spiro[indene-1,4'-piperidine]-1'-ylmethyl)thiazol-2-yl]methoxy]phenyl]hex-4-ynoate | 541 |
| 50 | Ethyl 3-[2-fluoro-4-[[4-methyl-5-(spiro[indene-1,4'-piperidine]-1'-ylmethyl)thiazol-2-yl]methoxy]phenyl]propanoate | 521 |
| 51 | Ethyl (3S)-3-[4-[[2-[(1-methylspiro[indoline-3,4'-piperidine]-1'-yl)methyl]thiazol-5-yl]methoxy]phenyl]hex-4-ynoate | 544 |
| 52 | Ethyl (3S)-3-[4-[[5-(spiro[indene-1,4'-piperidine]-1'-ylmethyl)thiazol-2-yl]methoxy]phenyl]hex-4-ynoate | 527 |
| 53 | Ethyl (3S)-3-[4-[[2-(Spiro[indene-1,4'-piperidine]-1'-ylmethyl)thiazol-5-yl]methoxy]phenyl]hex-4-ynoate | 527 |
| 54 | Ethyl (3S)-3-[4-[[5-[(1-methylspiro[indoline-3,4'-piperidine]-1'-yl]methyl]-2-thienyl]methoxy]phenyl]hex-4-ynoate | 543 |
| 55 | Ethyl 3-[2-fluoro-4-[[5-[(1-methylspiro[indoline-3,4'-piperidine]-1'-yl]methyl]-2-thienyl]methoxy]phenyl]propanoate | 523 |
| 56 | Ethyl (3S)-3-[4-[[4-methyl-5-(spiro[indene-1,4'-piperidine]-1'-ylmethyl)-2-thienyl]methoxy]phenyl]hex-4-ynoate | 540 |
| 57 | Ethyl (3S)-3-[4-[[4-methyl-5-(spiro[indane-1,4'-piperidine]-1'-ylmethyl)-2-thienyl]methoxy]phenyl]hex-4-ynoate | 542 |
| 58 | Ethyl 3-[2-fluoro-4-[[4-methyl-5-(spiro[indane-1,4'-piperidine]-1'-ylmethyl)-2-thienyl]methoxy]phenyl]propanoate | 522 |
| 59 | Ethyl 3-[2-fluoro-4-[[4-methyl-5-(spiro[indene-1,4'-piperidine]-1'-ylmethyl)-2-thienyl]methoxy]phenyl]propanoate | 520 |
| 60 | Ethyl 3-[2-fluoro-4-[[5-(spiro[indane-1,4'-piperidine]-1'-ylmethyl)-2-thienyl]methoxy]phenyl]propanoate | a |
| 61 | Ethyl (3S)-3-[4-[[5-(spiro[indane-1,4'-piperidine]-1'-ylmethyl)-2-thienyl]methoxy]phenyl]hex-4-ynoate | 528 |

-continued

| Prep. No. | Chemical Name | ESI/MS (m/z) (M + H) |
|---|---|---|
| 62 | Ethyl (3S)-3-[4-[[4-methyl-2-(spiro[indene-1,4'-piperidine]-1'-ylmethyl)thiazol-5-yl]methoxy]phenyl]hex-4-ynoate | 541 |
| 63 | Ethyl (3S)-3-[4-[[5-(spiro[indene-1,4'-piperidine]-1'-ylmethyl)-2-furyl]methoxy]phenyl]hex-4-ynoate | 510 |
| 64 | Ethyl 3-[4-[[5-[[(1Z,2Z)-2-allylidene-1-ethylidene-8-azaspiro[4.5]dec-3-en-8-yl]methyl]-2-thienyl]methoxy]-2-fluoro-phenyl]propanoate | b | a. ¹H-NMR (400 MHz, CDCl₃): δ 7.18-7.14 (m, 4H), 7.12-7.08 (m, 1H), 6.94-6.93 (d, J = 4 Hz, 1H), 6.82 (s, 1H), 6.70-6.66 (m, 2H), 5.12 (s, 2H), 4.14-4.09 (q, J = 4 Hz, 2H), 3.74 (s, 2H), 2.92-2.86 (m, 6H), 2.60-2.56 (m, 2H), 2.24-2.04 (m, 2H), 2.01-1.90 (m, 5H), 1.28-1.23 (m, 6H).
b. Crude product

Preparation 65

Ethyl (3S)-3-[4-[[5-(spiro[indene-1,4'-piperidine]-1'-ylmethyl)oxazol-2-yl]methoxy]phenyl]hex-4-ynoate

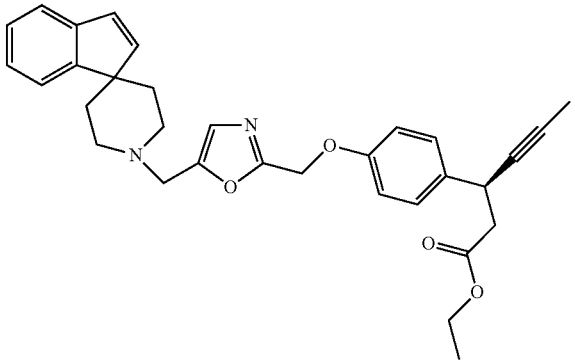 [SMILES: CC#C[C@@H](CC(=O)OCC)c1ccc(OCc2ncc(CN3CCC4(C=Cc5ccccc54)CC3)o2)cc1]

To a stirred solution of [5-(1'H-spiro[indene-1,4'-piperidin]-1'-ylmethyl)-1,3-oxazol-2-yl]methyl methanesulfonate (0.18 g, 0.48 mmol) in acetonitrile (10.0 mL) is added Cs₂CO₃ (0.39 g, 1.2 mmol) and ethyl (3S)-3-(4-hydroxyphenyl)hex-4-ynoate (0.13 g, 0.57 mmol). The reaction mixture is stirred at 80° C. for 1 hour and filtered through diatomaceous earth. The filtrate is evaporated to dryness and purified by silica gel chromatography, eluting with hexane:ethyl acetate (6.0:4.0) to give the title compound as a pale yellow oil (0.07 g, 28.2%). ESI/MS m/z 511.5 (M+1).

The following compound is prepared essentially as described by the method of preparation 65

| Prep. No. | Chemical Name | ESI/MS (m/z) (M + H) |
|---|---|---|
| 66 | Ethyl (3S)-3-[4-[[5-(spiro[indane-1,4'-piperidine]-1'-ylmethyl)oxazol-2-yl]methoxy]phenyl]hex-4-ynoate | 513 |

Preparation 67

Ethyl 3-[2-fluoro-4-[[4-methoxy-5-[(1-methylspiro[indoline-3,4'-piperidine]-1'-yl)methyl]-2-thienyl]methoxy]phenyl]propanoate

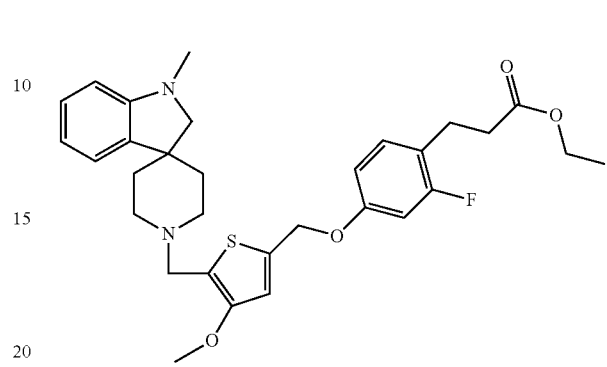

To a solution at 0° C. of ethyl 3-[2-fluoro-4-[(5-formyl-4-methoxy-2-thienyl)methoxy]phenyl]propanoate (0.4 g, 1.0 mmol) in methanol, is added 1-methylspiro[indoline-3,4'-piperidine (0.258 g, 1.0 mmol), and NaCNBH₃ (0.273 g, 4.3 mmol). The reaction mixture is warmed to room temperature and stirred for 12 hours. The mixture is diluted with water (15 mL) and extracted with ethyl acetate. The organic layer is washed with water (10 mL) and brine (10 mL), dried over sodium sulfate, filtered, and concentrated. The crude material is purified by preparative TLC to give the title compound as a colorless liquid (0.2 g, 33%). ESI/MS m/z 553.2 (M+H)⁺.

The following compound is prepared essentially as described by the method of preparation 67

| Prep. No. | Chemical Name | ESI/MS (m/z) (M + H) |
|---|---|---|
| 68 | Ethyl 3-[2-fluoro-4-[[4-methoxy-5-(spiro[indane-1,4'-piperidine]-1'-ylmethyl)-2-thienyl]methoxy]phenyl]propanoate | 538 |

Example 1

(3S)-3-[4-[[5-(Spiro[indene-1,4'-piperidine]-1'-ylmethyl)-2-thienyl]methoxy]phenyl]hex-4-ynoic acid Method A

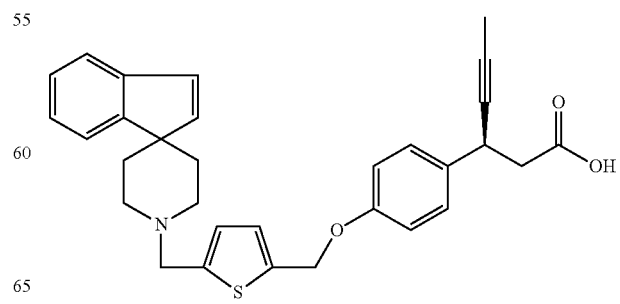

To a solution of ethyl (3S)-3-[4-[[5-(spiro[indene-1,4'-piperidine]-1'ylmethyl)-2-thienyl]methoxy]phenyl]hex-4-ynoate (1.1 g, 2.0 mmol) in ethanol (6 mL) is added 5M NaOH (0.83 mL, 4.1 mmol) and the mixture is reacted under microwave conditions for 5 minutes at 90° C. The mixture is concentrated, dissolved in water, acidified with 2N HCl, and extracted with chloroform (2×50 mL). The combined extracts are washed with saturated NaHCO$_3$ (2×5 mL), NH$_4$Cl (2×5 mL), water (2×5 mL) and saturated brine (2×5 mL), dried over sodium sulfate, filtered, and concentrated to give the title compound as an off-white solid (0.746 g, 71%). $^1$HNMR (DMSO d$_6$, 400 MHz) δ 12.2 (bs, 1H), 7.43-7.41 (d, J=7.2 Hz, 1H), 7.31-7.25 (dd, J=6.8 Hz, 3H), 7.21-7.13 (m, J=7.2 Hz, 2H), 7.02-7.01 (d, J=3.2 Hz, 1H), 6.96-6.94 (d, J=8.4 Hz, 1H), 6.92-6.90 (d, J=5.6 Hz, 1H), 6.88-6.87 (d, J=2.8 Hz, 1H) 6.77-6.76 (d, J=5.2 Hz, 1H) 5.19 (s, 2H), 3.94 (s, 1H), 3.76 (s, 2H), 2.94-2.901 (t, J=11.2 Hz, 2H), 2.59-2.57 (d, J=7.6 Hz, 2H), 2.41-2.36 (t, J=11.2 Hz, 2H), 2.08-2.03 (t, J=10.4 Hz, 2H), 1.76 (s, 3H), 1.22 (s, 2H), ESI/MS m/z 498 (M+H)$^+$.

Method B

Ethyl (3S)-3-[4-[[5-(spiro[indene-1,4'-piperidine]-1'ylmethyl)-2-thienyl]methoxy]phenyl]hex-4-ynoate (33.0 g, 62.7 mol) is dissolved in ethanol (600 mL) and the mixture is cooled to 10-15° C. 5 M NaOH (5.02 g, 125.5 mmol) is slowly added and the mixture stirred for 10 min followed by heating to 80° C. for 2 hours. The solvent is evaporated and the mixture is dissolved in a minimum amount of water. The pH is adjusted to ~7.0 with 1N HCl solution. The solution is extracted with ethyl acetate (2×300 mL) washed with brine, dried over sodium sulfate and evaporated to dryness. To the crude material is added methyl t-butyl ether (300 mL) and 0.2% of methanol and the mixture is stirred for 30 minutes. The resultant precipitate is filtered and dried under vacuum at 48° C. to give the title compound as cream colored solid (24.0 g, 76%). $^1$H NMR (DMSO-d$_6$) δ 12.217 (s, 1H), 7.438-7.421 (d, 1H), 7.330-7.271 (m, 3H), 7.228-7.126 (m, 2H), 7.046-7.039 (d, 1H), 6.978-6.906 (m, 4H), 6.795-6.781 (d, 1H), 5.213 (s, 2H), 3.972-3.928 (m, 1H), 3.788 (bs, 2H), 2.945 (m, 2H), 2.608-2.589 (d, 2H), 2.422 (m, 2H), 2.107-2.051 (m, 2H), 1.778-1.772 (s, 3H), 1.233-1.148 (m, 2H).

The following compounds are prepared essentially as described by the method of Example 1 (Method A)

| Ex No. | Chemical Name | Structure | ESI/MS (m/z) (M + H) |
|---|---|---|---|
| 2 | (3S)-3-[4-[[5-[(1-Methylspiro[indoline-3,4'-piperidine]-1'-yl)methyl]-2-furyl]methoxy]phenyl]hex-4-ynoic acid | 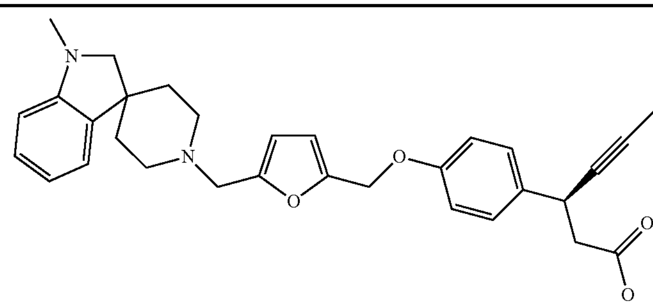 | 499 |
| 3 | (3S)-3-[4-[[5-(Spiro[indane-1,4'-piperidine]-1'-ylmethyl)oxazol-2-yl]methoxy]phenyl]hex-4-ynoic acid | 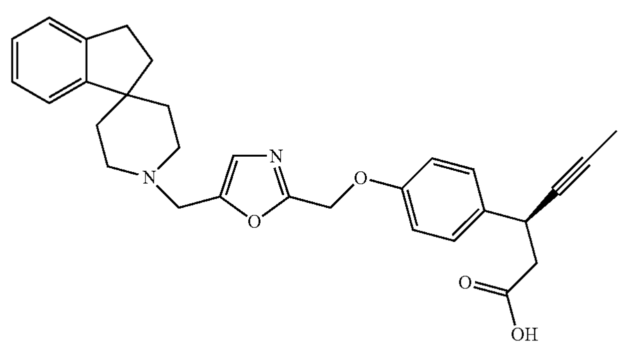 [SMILES: CC#C[C@@H](CC(=O)O)c1ccc(OCc2ncc(CN3CCC4(CCc5ccccc54)CC3)o2)cc1] | 485 |
| 4 | (3S)-3-[4-[[5-(Spiro[indene-1,4'-piperidine]-1'-ylmethyl)oxazol-2-yl]methoxy]phenyl]hex-4-ynoic acid | 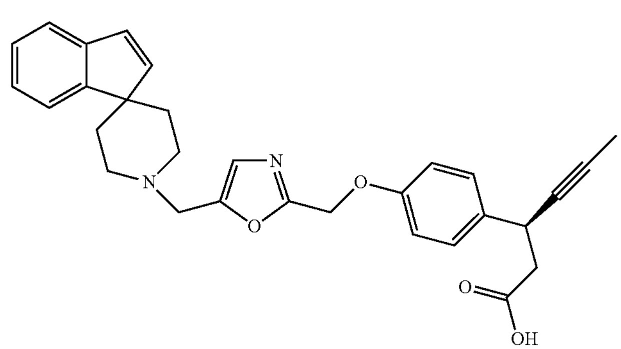 [SMILES: CC#C[C@@H](CC(=O)O)c1ccc(OCc2ncc(CN3CCC4(C=Cc5ccccc54)CC3)o2)cc1] | 483 |

| Ex No. | Chemical Name | Structure | ESI/MS (m/z) (M + H) |
|---|---|---|---|
| 5 | 3-[2-Fluoro-4-[[5-(spiro[indene-1,4'-piperidine]-1'-ylmethyl)-2-furyl]methoxy]phenyl]propanoic acid | 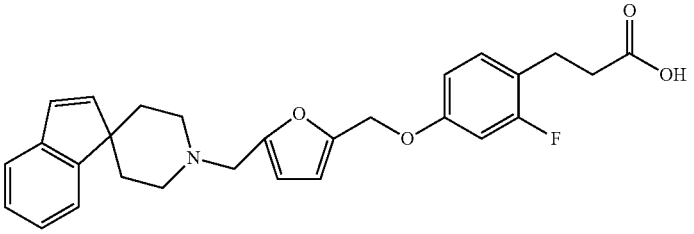 [SMILES: O=C(O)CCc1ccc(OCc2ccc(CN3CCC4(C=Cc5ccccc54)CC3)o2)cc1F] | 461 |
| 6 | (3S)-3-[4-[[2-(Spiro[indane-1,4'-piperidine]-1'-ylmethyl)thiazol-5-yl]methoxy]phenyl]hex-4-ynoic acid | 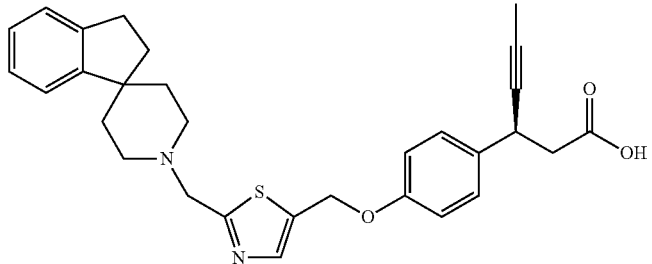 [SMILES: CC#C[C@@H](CC(=O)O)c1ccc(OCc2cnc(CN3CCC4(CCc5ccccc54)CC3)s2)cc1] | 501 |
| 7 | (3S)-3-[4-[[4-Methyl-5-(spiro[indene-1,4'-piperidine]-1'-ylmethyl)thiazol-2-yl]methoxy]phenyl]hex-4-ynoic acid | 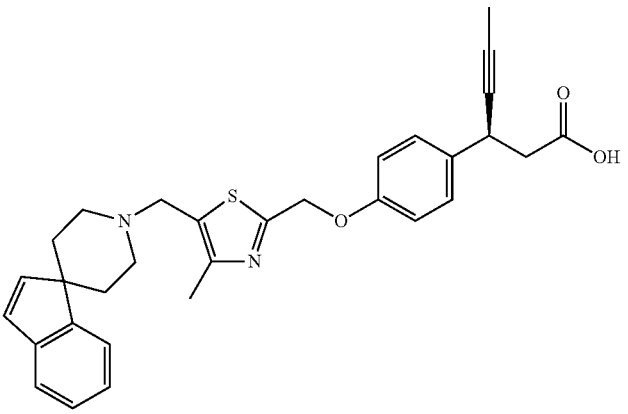 [SMILES: CC#C[C@@H](CC(=O)O)c1ccc(OCc2nc(C)c(CN3CCC4(C=Cc5ccccc54)CC3)s2)cc1] | 513 |
| 8 | 3-[2-Fluoro-4-[[4-methyl-5-(spiro[indene-1,4'-piperidine]-1'-ylmethyl)thiazol-2-yl]methoxy]phenyl]propanoic acid | 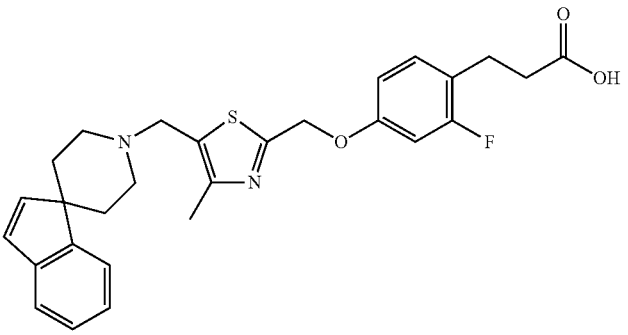 [SMILES: Cc1nc(COc2ccc(CCC(=O)O)c(F)c2)sc1CN1CCC2(C=Cc3ccccc32)CC1] | 493 |

| Ex No. | Chemical Name | Structure | ESI/MS (m/z) (M + H) |
|---|---|---|---|
| 9 | (3S)-3-[4-[[2-[(1-Methylspiro[indoline-3,4'-piperidine]-1'-yl)methyl]thiazol-5-yl]methoxy]phenyl]hex-4-ynoic acid | 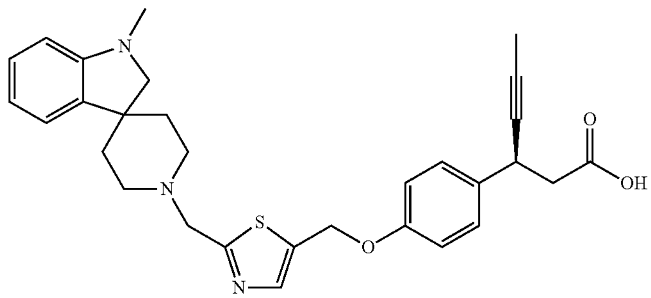 [SMILES: CC#C[C@@H](CC(=O)O)c1ccc(OCc2cnc(CN3CCC4(CC3)CN(C)c3ccccc34)s2)cc1] | 516 |
| 10 | (3S)-3-[4-[[5-(Spiro[indene-1,4'-piperidine]-1'-ylmethyl)thiazol-2-yl]methoxy]phenyl]hex-4-ynoic acid | 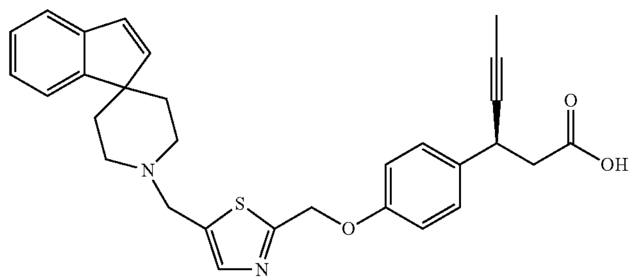 [SMILES: CC#C[C@@H](CC(=O)O)c1ccc(OCc2ncc(CN3CCC4(C=Cc5ccccc54)CC3)s2)cc1] | 499 |
| 11 | (3S)-3-[4-[[2-(Spiro[indene-1,4'-piperidine]-1'-ylmethyl)thiazol-5-yl]methoxy]phenyl]hex-4-ynoic acid | 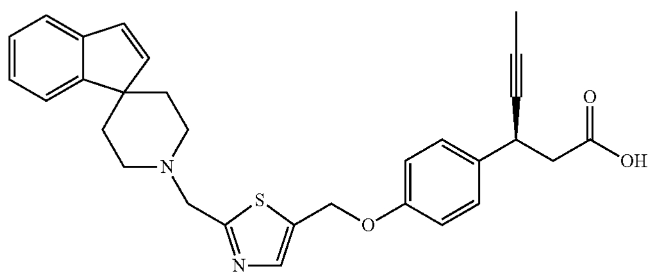 [SMILES: CC#C[C@@H](CC(=O)O)c1ccc(OCc2cnc(CN3CCC4(C=Cc5ccccc54)CC3)s2)cc1] | 499 |
| 12 | (3S)-3-[4-[[5-[(1-Methylspiro[indoline-3,4'-piperidine]-1'-yl)methyl]-2-thienyl]methoxy]phenyl]hex-4-ynoic acid | 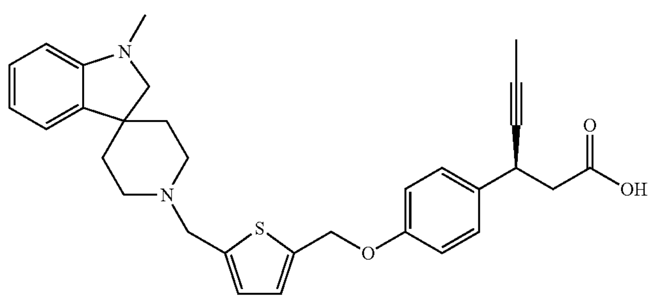 [SMILES: CC#C[C@@H](CC(=O)O)c1ccc(OCc2ccc(CN3CCC4(CC3)CN(C)c3ccccc34)s2)cc1] | 515 |
| 13 | 3-[2-Fluoro-4-[[5-[(1-methylspiro[indoline-3'4'-piperidine]-1'-yl)methyl]-2-thienyl]methoxy]phenyl]propanoic acid | 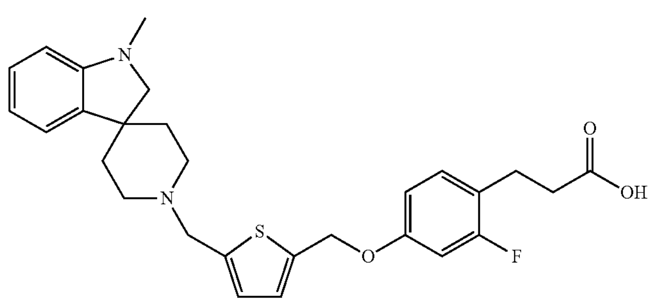 [SMILES: CN1CC2(CCN(Cc3ccc(COc4ccc(CCC(=O)O)c(F)c4)s3)CC2)c2ccccc21] | 495 |

-continued

| Ex No. | Chemical Name | Structure | ESI/MS (m/z) (M + H) |
|---|---|---|---|
| 14 | (3S)-3-[4-[[4-Methyl-5-(spiro[indene-1,4'-piperidine]-1'-ylmethyl)-2-thienyl]methoxy]phenyl]hex-4-ynoic acid | 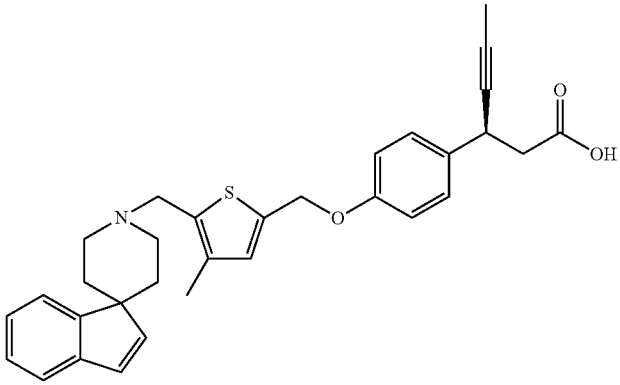 [SMILES: CC#C[C@@H](CC(=O)O)c1ccc(OCc2cc(C)c(CN3CCC4(C=Cc5ccccc54)CC3)s2)cc1] | 512 |
| 15 | (3S)-3-[4-[[4-Methyl-5-(spiro[indane-1,4'-piperidine]-1'-ylmethyl)-2-thienyl]methoxy]phenyl]hex-4-ynoic acid | 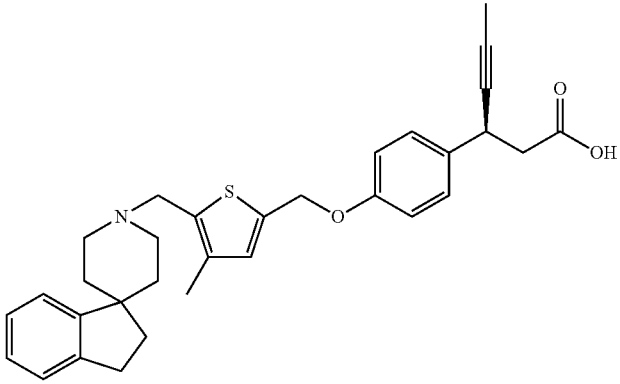 [SMILES: CC#C[C@@H](CC(=O)O)c1ccc(OCc2cc(C)c(CN3CCC4(CCc5ccccc54)CC3)s2)cc1] | 514 |
| 16 | 3-[2-Fluoro-4-[[4-methyl-5-(spiro[indane-1,4'-piperidine]-1'-ylmethyl)-2-thienyl]methoxy]phenyl]propanoic acid | 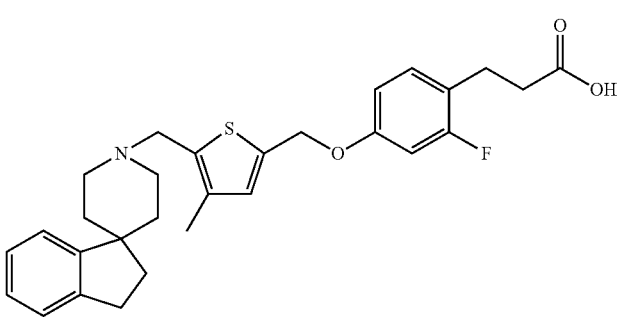 [SMILES: Cc1cc(COc2ccc(CCC(=O)O)c(F)c2)sc1CN1CCC2(CCc3ccccc32)CC1] | 494 |
| 17 | 3-[2-Fluoro-4-[[4-methyl-5-(spiro[indene-1,4'-piperidine]-1'-ylmethyl)-2-thienyl]methoxy]phenyl]propanoic acid | 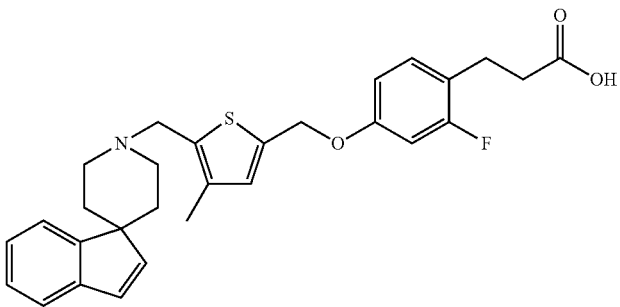 [SMILES: Cc1cc(COc2ccc(CCC(=O)O)c(F)c2)sc1CN1CCC2(C=Cc3ccccc32)CC1] | 492 |

-continued

| Ex No. | Chemical Name | Structure | ESI/MS (m/z) (M + H) |
|---|---|---|---|
| 18 | 3-[2-Fluoro-4-[[5-(spiro[indane-1,4'-piperidine]-1'-ylmethyl)-2-thienyl]methoxy]phenyl]propanoic acid | 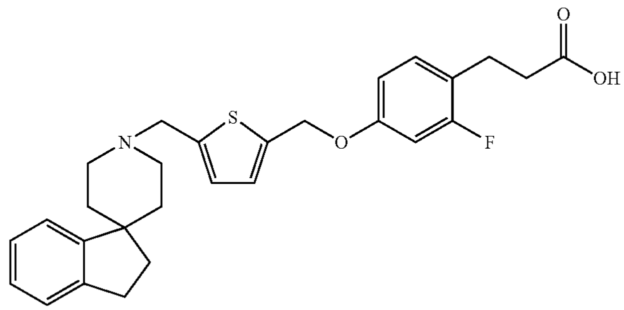 [SMILES: O=C(O)CCc1ccc(OCc2ccc(CN3CCC4(CCc5ccccc54)CC3)s2)cc1F] | 478 |
| 19 | (3S)-3-[4-[[5-(Spiro[indane-1,4'-piperidine]-1'-ylmethyl)-2-thienyl]methoxy]phenyl]hex-4-ynoic acid | 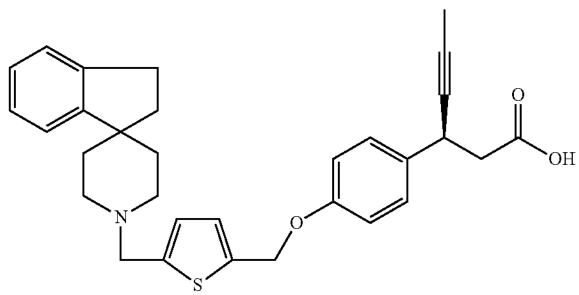 [SMILES: CC#C[C@@H](CC(=O)O)c1ccc(OCc2ccc(CN3CCC4(CCc5ccccc54)CC3)s2)cc1] | 500 |
| 20 | (3S)-3-[4-[[4-Methyl-2-(Spiro[indene-1,4'-piperidine]-1'-ylmethyl)thiazol-5-yl]methoxy]phenyl]hex-4-ynoic acid | 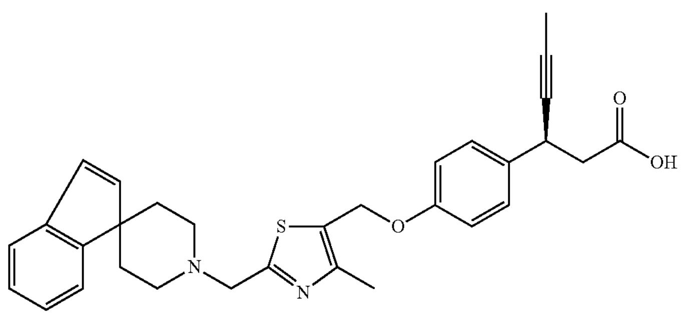 [SMILES: CC#C[C@@H](CC(=O)O)c1ccc(OCc2sc(CN3CCC4(C=Cc5ccccc54)CC3)nc2C)cc1] | 513 |
| 21 | (3S)-3-[4-[[5-(Spiro[indene-1,4'-piperidine]-1'-ylmethyl)-2-furyl]methoxy]phenyl]hex-4-ynoic acid | 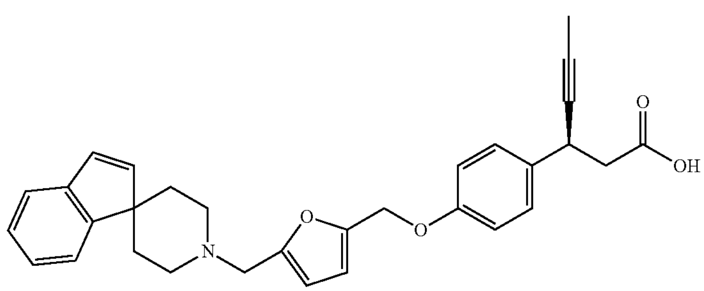 [SMILES: CC#C[C@@H](CC(=O)O)c1ccc(OCc2ccc(CN3CCC4(C=Cc5ccccc54)CC3)o2)cc1] | 482 |
| 22 | 3-[2-Fluoro-4-[[5-(spiro[indene-1,4'-piperidine]-1'-ylmethyl)-2-thienyl]methoxy]phenyl]propanoic acid | 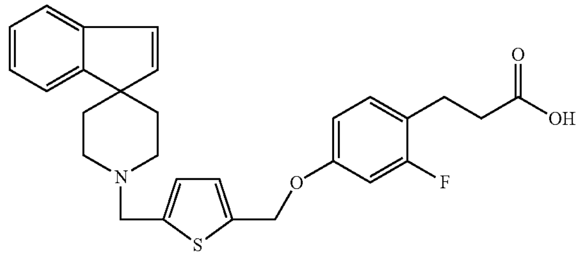 [SMILES: O=C(O)CCc1ccc(OCc2ccc(CN3CCC4(C=Cc5ccccc54)CC3)s2)cc1F] | 478 |

-continued

| Ex No. | Chemical Name | Structure | ESI/MS (m/z) (M + H) |
|---|---|---|---|
| 23 | 3-[2-Fluoro-4-[[4-methoxy-5-[(1-methylspiro[indoline-3,4'-piperidine]-1'-yl)methyl]-2-thienyl]methoxy]phenyl]propanoic acid | 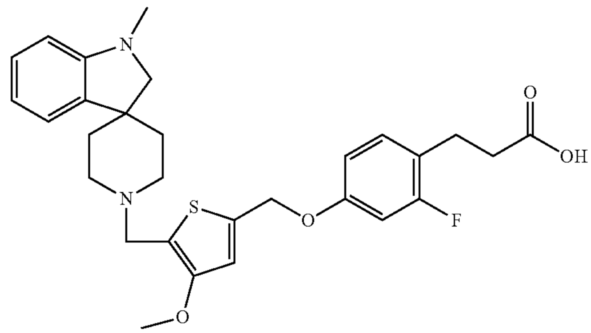 [SMILES: COc1cc(COc2ccc(CCC(=O)O)c(F)c2)sc1CN1CCC2(CC1)CN(C)c1ccccc12] | 525 |
| 24 | 3-[2-Fluoro-4-[[4-methoxy-5-(spiro[indane-1,4'-piperidine]-1'-ylmethyl)-2-thienyl]methoxy]phenyl]propanoic acid | 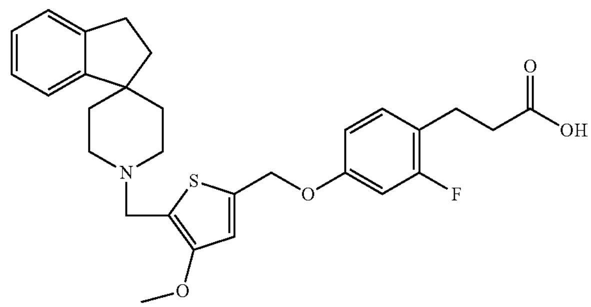 [SMILES: COc1cc(COc2ccc(CCC(=O)O)c(F)c2)sc1CN1CCC2(CCc3ccccc32)CC1] | 510 |

The causes of T2D are believed to be two-fold, insulin resistance, and progressive failure of pancreatic beta cells to produce adequate amounts of insulin to lower circulating glucose levels. Insulin resistance develops when normal insulin levels are unable to dispose of circulating plasma glucose into target tissues, including skeletal muscle and adipose tissue. As the pancreas produces more insulin to compensate for the excessively high glucose levels due to insulin resistance, the pancreatic beta cells eventually become exhausted and no additional insulin is available for secretion. Over time, the pancreatic beta cells completely fail and a person with T2D becomes similar to one with type 1 diabetes. High levels of circulating glucose is the hallmark of diabetes and can eventually lead to serious complications such as heart disease and strokes, high blood pressure, blindness, kidney and nerve damage, infections, and gum disease. Therefore, it is important to control and treat T2D as early as possible with exercise; a proper diet; oral anti-diabetic therapies; and eventually with insulin. Compounds claimed by the present invention provide additional pharmacological treatment options. Compounds selectively modulating GPR40 may be particularly desirable.

GPR40: Information

Results of studies using transgenic mice over-expressing the human GPR40 gene under control of the insulin II promoter recently reported by Nagasumi further support that GPR40 plays an important role in the regulation of GDIS and plasma glucose levels in-vivo, especially in rodent models of insulin resistance. Nagasumi K, et. al., *Overexpression of GPR40 in pancreatic β-cells augments glucose-stimulated insulin secretion and improves glucose tolerance in normal and diabetic mice* Diabetes 58: 1067-1076, 2009. See also, Briscoe CP et al. *The orphan G protein-coupled receptor GPR40 is activated by medium and long chain fatty acids*, Journal Biological Chemistry 278: 11303-11311, 2003. These findings further support that the development of new GPR40 modulator compounds may be particularly desired for use in the treatment of T2D.

Calcium Flux Primary Assay

The compounds exemplified herein are tested essentially as described below and exhibit an $EC_{50}$ value for the Calcium Flux Primary assay of lower than 1 μM.

This assay is used to screen compounds by measuring the increase in intracellular calcium levels that results when a ligand binds and activates GPR40, thus demonstrating the potency and efficacy of GPR40 agonists. HEK293 cells over expressing the human GPR40 cDNA maintained in Dulbecco's modified Eagle's medium with F12 medium in 3:1 ratio supplemented with 10% FBS and 800 μg/ml geneticin at 37° C. and 5% $CO_2$ are employed for the study. Agonist assays are performed using a Calcium 4 Dye assay kit (Molecular Devices) in the presence (0.1%) or absence of fatty acid free BSA in the assay buffer (1×HBSS (Hank's Balanced Salt Solution) & 20 mM HEPES (4-(2-hydroxyethyl)-1-piperazineethanesulfonic acid). Receptor activation is measured as an increase in intracellular calcium using the Fluorometric Imaging Plate Reader (FLIPR). Maximum change in fluorescence over the base line is used to determine agonist response. $EC_{50}$ (effective concentration at half the maximal response) value of the compound is calculated using Excel Fit software (version 4; IDBS) by plotting concentration vs relative fluorescence units (RFUs). Percent efficacy is calculated based on the maximal response exhibited by compound compared to the natural ligand, linoleic acid. The test compound of Example 1 has an $EC_{50}$ of 114+/−93 nM with 91+/−9% efficacy when examined in this assay. These results further demonstrate the desired potency and efficacy as GPR40 agonists.

Glucose Dependent Insulin Secretion (GDIS) Assays

Because activation of GPR40 is known to result in insulin secretion which is dependent on high glucose concentrations, two separate assay systems (insulinoma cell line and primary rodent islets) are developed to further characterize compounds that are known to increase intracellular calcium in the GPR40 primary assay discussed above.

GDIS assays are performed using the mouse insulinoma cell line Min6. Min6 cells are maintained in Dulbecco's Modified Eagle's Medium (DMEM) containing non-essential amino acids, 10% FBS, 50 mM 2-mercaptoethanol and 1% penicillin and streptomycin at 37° C. plus 5% $CO_2$ On the day of the experiment, the cells are washed twice with 200 µl of pre-warmed Krebs-ringer buffer without glucose. Addition of 200 µL of pre-warmed Krebs-ringer buffer containing 2.5 mM glucose is used to starve the cells followed by the addition of compounds in the presence of a high concentration of glucose (25 mM). The plate is incubated at 37° C. for 2 hours. At the end of the 2 h incubation, the supernatant is gently transferred into a Millipore filter plate and spun at 200 g (gravitational force) for 3 minutes. Insulin is assayed using a Mercodia Insulin estimation kit. Addition of Example 1 at 1 µM plus 25 mM glucose to the Min6 cells resulted in a statistically significant, two-fold increase in insulin secretion compared to that achieved with 25 mM glucose alone.

GDIS assays using primary rodent pancreatic islets of Langerhans are also used to characterize exemplified compounds. Pancreatic islets are isolated from male SD (Sprague Dawley) rats by collagenase digestion and Histopaque density gradient separation. The islets are cultured overnight in RPMI-1640 medium with GlutaMAXn (stabilized, dipeptide form of L-glutamine (Invitrogen catalog #61870-010)) to facilitate recovery from the isolation process. Insulin secretion is determined by a 90 minute incubation in EBSS (Earle's Balances Salt Solution) buffer in a 48-well plate. Briefly, islets are first preincubated in EBSS with 2.8 mM glucose for 30 min and are then transferred to a 48-well plate (four islets/well) containing 150 µl 2.8 mM glucose and incubated with 150 µl of EBSS with 2.8 or 11.2 mM glucose in the presence or absence of test compounds for 90 minutes. The buffer is removed from the wells at the end of the incubation and assayed for insulin levels using the Rat Insulin ELISA kit (Mercodia). In this assay system, administration of Example 1 at different concentrations results in a 2- to 4-fold increase in insulin compared to that achieved with 11.2 mM glucose alone.

Selectivity Assays:

Peroxisome Proliferator-Activated Receptor (PPAR) α, δ, and γ Binding and Functional Assays:

Because GPR40 is known to be activated by ligands to PPARγ exemplified compounds are examined in PPARα, PPARδ, and PPARγ binding and functional assays to determine the selectivity of exemplified compounds for GPR40. Compounds exemplified herein are tested essentially as described below for PPAR binding and generally have binding values greater than 1000 nM with 10 µM concentrations of test compound and are thus considered negative for PPAR activity.

Binding affinities of compounds for the PPAR α, δ, and γ receptors are assessed using Scintillation Proximity Assay (SPA) technology. Biotinylated oligonucleotide Direct Repeat 2 (DR2) is used for binding the receptors to Yttrium silicate streptavidin-coated SPA beads. PPAR α, δ, γ and retinoid X receptor (RXR) α are over expressed in HEK293 cells, and cell lysates containing the specific receptors are used in the individual assays. The DR2 is attached to the SPA beads over a 30 minute period in a binding buffer containing 10 mM HEPES pH 7.8, 80 mM KCl, 0.5 mM $MgCl_2$, 1 mM DTT, 0.5% 3[(3-cholamidopropyl)dimethylammonio]-propanesulfonic acid (CHAPS), and 4.4% bovine serum. The cell lysates are incubated in each well with one of 11 concentrations of compound in the presence of a radio-labeled (~0.033.8 µCi $^3$H) PPAR α/δ dual agonist reference compound for the alpha and delta receptor assays and a radio-labeled (~0.037.3 µCi$^3$H) PPARγ agonist reference compound for the gamma receptor assays, 110.3 µg of Yttrium SPA Streptavidin coated beads, 0.126 nM HD Oligo DR2, and either 0.3 µg PPARα with 0.5 µg RXRα, 0.5 µg PPARδ with 0.5 µg RXRα, or 1.25 µg PPARγ with 3.03 µg RXRα in the binding buffer above plus 14% glycerol and 5 µg of sheared salmon sperm DNA. Non-specific binding is determined in the presence of 10,000 nM of the unlabeled PPAR α/δ dual agonist reference compound for the alpha and delta receptor assays and the PPARγ agonist reference compound for the gamma receptor assay. The binding reaction (100 µl per well in a 96 well [Costar 3632] plate) is incubated for 10 h and counted disintegration per minutes (dpm) on a Wallac Microbeta. Receptor binding affinity ($IC_{50}$) for the compounds is determined by fitting an 11 point concentration-response curve with a 4-paramater logistic equation. K, is determined from the $IC_{50}$ using the Cheng-Prussoff equation and Kd determined by saturation binding. For the compound of Example 1, no binding is detected in any of the three PPAR binding assays with concentrations up to 10 µM. Thus, the assays set forth herein support that the compound of Example 1 selectively activates GPR40 while avoiding the undesired PPAR activity. Exemplified compounds relative $IC_{50}$, are generally greater than 10 µM for the PPAR isoforms, supporting that the compounds avoid PPAR activity while providing the desired GPR40 activation.

Gal4 PPARα, Gal4 PPARδ, and PPARγ reporter functional assays are also used to monitor the selectivity of exemplified compounds. CV1 cells, which are derived from the renal tissue of an African green monkey, are transfected with various receptor and reporter plasmids using Fugene. For the Gal4 PPARα and PPARδ assays, a reporter plasmid containing five tandem copies of the yeast transcription protein Gal4 response element, cloned upstream of a firefly luciferase gene driven by the major late promoter of adenovirus, is transfected together with a Simian Virus 40 (SV40) driven plasmid constitutively expressing a hybrid protein containing the Gal4 DNA binding domain (DBD), and either the PPARα or PPARδ ligand binding. For the PPARγ assay, plasmids encoding PPARγ and RXRα, both driven by a cytomegalovirus (CMV) promoter are transfected together with a plasmid containing luciferase reporter cDNA driven by the TK promoter and a receptor response element (2×PPRE). Cells are transfected in T225 $cm^2$ cell culture flasks in DMEM media with 5% charcoal-stripped FBS. After an overnight incubation, transfected cells are trypsinized, plated in opaque 96 well dishes (15,000 cells/well) in DMEM media containing 5% charcoal-stripped FBS, incubated for 4 h, and exposed to 0.17 ηM to 10 µM of test compounds or reference compound in half log dilutions. After 24 hours incubation with compounds, cells are lysed and luciferase activity is determined as a measure of receptor activation by luminescence. Data are fitted to a four parameter-fit logistics model to determine $EC_{50}$ values. The maximum percent stimulation is determined versus maximum stimulation obtained with 10 µM of an appropriate PPAR agonist reference compound. No functional activation of PPARα, PPARδ, or PPARγ is detected with the compound of Example 1 when examined up to 10 µM in the specific PPAR co-transfection (CTF)/functional assays described above. Thus, the assay supports that the exemplified compounds avoid PPAR agonist activity, as desired.

In Vivo Efficacy: Intraperitoneal Glucose Tolerance Test (IP-GTT)

To examine the ability of exemplified compounds to activate GPR40 in-vivo resulting in anti-diabetic efficacy, i.e. an increase in insulin and reduction in glucose levels, a 4-day intraperitoneal glucose tolerance test (ipGTT) study is completed with each compound tested in the IPGTT.

Male Balb/c (Albino mice) mice (8-9 weeks of age) are single housed and fed with normal rodent chow diet and water ad libitum. Animals are weighed and randomized by body weight and daily body weights are recorded. Upon study initiation, animals are dosed once per day orally for three days using a formulation carrying methylcellulose and tween-80. On the night before the 4-day IPGTT study, animals are fasted overnight in clean cages. On the morning of the IPGTT (Day 4), animals are dosed orally with compound or vehicle alone 60 minutes prior to the IPGTT (glucose 2 g/kg, i.p.). Blood glucose levels are determined from tail bleeds taken at 0, 3, 7, 15, 30, and 60 min after glucose challenge. Plasma is isolated and used to estimate respective insulin levels. The blood glucose excursion profile from t=0 to t=60 min is used to integrate an area under the curve (AUC) for each treatment. Percent lowering in glucose is calculated from the AUC data of the compounds with respect to the AUC of vehicle group. The test compound is orally administered at 0.1, 0.3, 1.0, 3.0, or 10 mg/kg, and a positive control is administered at 10 mg/kg. No concentration of the compound of Example 1 or the positive control significantly lowered glucose levels at the 3 minute time point during the GTT. In contrast, glucose levels are significantly lowered with the 0.3, 1.0, 3.0, and 10 mg/kg doses of the compound of Example 1 and the positive control at the 7 minute time point and with 0.1, 0.3, 1.0, and 3.0 mg/kg doses of the compound of Example 1 at the 15, 30, and 60 minute time points. The positive control significantly lowered glucose levels at the 30 and 60 min time points. The $ED_{50}$ for the compound of Example 1 based on AUCs for glucose lowering is 0.21 mg/kg. In this study, insulin levels were significantly elevated at the 3.0 and 10.0 mg/kg dose of the compound of Example 1 which is consistent with activation of GPR40. The results of this study demonstrate that activation of GPR40 by Example 1 leads to in-vivo anti-diabetic efficacy.

We claim:

1. A compound of the formula:

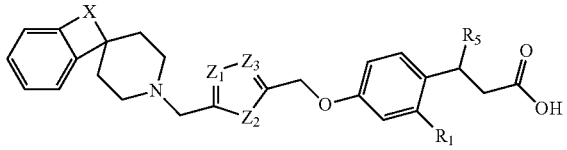

or a pharmaceutically acceptable salt thereof;
wherein:
$R_1$ is selected from the group consisting of H, F and Cl;
$R_5$ is H or —C≡CCH$_3$;
X is selected from the group consisting of —CH$_2$CH$_2$—, —CH=CH—, and —N(R$_7$)CH$_2$—;
$R_7$ is selected from the group consisting of H and $C_{1-3}$alkyl;
$Z_1$ is selected from the group consisting of —C(R$_3$)— and —N—;
$R_3$ is selected from the group consisting of H, OCH$_3$, and CH$_3$;

$Z_2$ is selected from the group consisting of —S— and —O—;
$Z_3$ is selected from the group consisting of —C(R$_4$)— and —N—;
$R_4$ is selected from the group consisting of H, OCH$_3$, and CH$_3$; and—
wherein at least one selected from the group consisting of $Z_1$ and $Z_3$ is —C(R$_3$)— or —C(R$_4$)—.

2. A compound or salt thereof as claimed by claim 1 wherein $R_1$ is H.

3. A compound or salt thereof as claimed by claim 1 wherein $R_5$ is —C≡CCH$_3$.

4. A compound or salt thereof as claimed by claim 3 wherein the compound is the S isomer.

5. A compound or salt thereof as claimed by claim 1 wherein $R_1$ is F and $R_5$ is H.

6. A compound as claimed by claim 1 wherein $Z_2$ is —S—.

7. A compound or salt thereof as claimed by claim 1 wherein $Z_1$ is —C(R$_3$)—.

8. A compound or salt thereof as claimed by claim 7 wherein $R_3$ is H or CH$_3$.

9. A compound or salt thereof as claimed by claim 1 wherein $Z_3$ is —C(R$_4$)—.

10. A compound or salt thereof as claimed by claim 9 wherein $R_4$ is H.

11. A compound or salt thereof as claimed by claim wherein X is —CH=CH—.

12. A compound or salt thereof as claimed by claim 1 wherein X is —N(R$_7$)CH$_2$—.

13. A compound or salt thereof as claimed by claim 12 wherein $R_7$ is CH$_3$.

14. A pharmaceutically acceptable salt as claimed by claim 1.

15. A compound of the formula

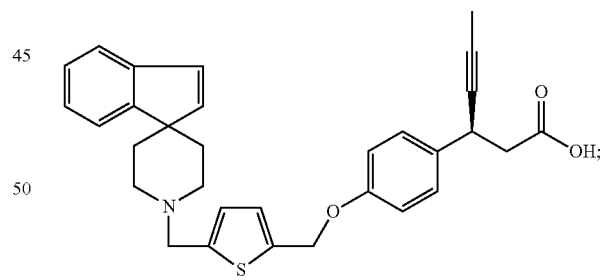

or a pharmaceutically acceptable salt thereof.

16. A pharmaceutical composition comprising a pharmaceutically acceptable carrier and a compound as claimed by claim 1 or a pharmaceutically acceptable salt thereof.

17. A method for treating type 2 diabetes in a mammal, comprising the step of administering to the mammal a compound as claimed by claim 1 or a pharmaceutically acceptable salt thereof.

18. A compound of the formula

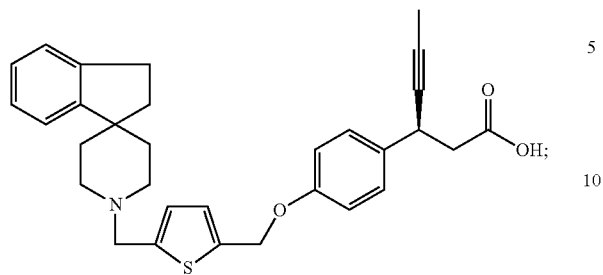

or a pharmaceutically acceptable salt thereof.

19. A pharmaceutical composition comprising a pharmaceutically acceptable carrier and a compound as claimed by claim 18 or a pharmaceutically acceptable salt thereof.

20. A method for treating type 2 diabetes in a mammal, comprising the step of administering to the mammal a compound as claimed by claim 18 or a pharmaceutically acceptable salt thereof.

* * * * *

UNITED STATES PATENT AND TRADEMARK OFFICE
CERTIFICATE OF CORRECTION

PATENT NO.        : 8,822,486 B2  
APPLICATION NO.   : 13/505470  
DATED             : September 2, 2014  
INVENTOR(S)       : Chafiq Hamdouchi et al.

It is certified that error appears in the above-identified patent and that said Letters Patent is hereby corrected as shown below:

On the Title Page

On the first page, column 2 Item 56 (Other Publications), line 2, please delete "eceptor" and insert --receptor--, therefor.

In the Claims

In Column 40, line 7, in Claim 1, please delete "and-" and insert --and--, therefor.

In Column 40, line 31, in Claim 11, after "claim" insert --1--, therefor.

Signed and Sealed this  
Tenth Day of February, 2015

Michelle K. Lee  
*Deputy Director of the United States Patent and Trademark Office*